(12) United States Patent
Putnam et al.

(10) Patent No.: US 10,252,263 B2
(45) Date of Patent: *Apr. 9, 2019

(54) MICROFLUIDIC DEVICES AND METHODS OF MANUFACTURE AND USE

(71) Applicant: CyVek, Inc., Wallingford, CT (US)

(72) Inventors: Martin A. Putnam, Cheshire, CT (US); Jeffrey T. Branciforte, Hartford, CT (US); Charles O. Stanwood, Durham, CT (US)

(73) Assignee: CyVek, Inc., Wallingford, CT (US)

( * ) Notice: Subject to any disclaimer, the term of this patent is extended or adjusted under 35 U.S.C. 154(b) by 546 days.

This patent is subject to a terminal disclaimer.

(21) Appl. No.: 14/955,785

(22) Filed: Dec. 1, 2015

(65) Prior Publication Data
US 2016/0158750 A1  Jun. 9, 2016

Related U.S. Application Data

(60) Division of application No. 13/427,875, filed on Mar. 22, 2012, now Pat. No. 8,871,529, and a (Continued)

(51) Int. Cl.
*B29C 65/00* (2006.01)
*B29C 65/02* (2006.01)
(Continued)

(52) U.S. Cl.
CPC ... *B01L 3/502707* (2013.01); *B01L 3/502715* (2013.01); *B01L 3/502738* (2013.01);
(Continued)

(58) Field of Classification Search
CPC ....... B29C 65/00; B29C 65/006; B29C 66/00; B29C 66/026; B29C 66/028;
(Continued)

(56) References Cited

U.S. PATENT DOCUMENTS

| 4,320,087 A | 3/1982 | Chau et al. |
| 4,657,869 A | 4/1987 | Richards et al. |

(Continued)

FOREIGN PATENT DOCUMENTS

| EP | 0 475 303 A2 | 3/1992 |
| WO | 01/16004 A1 | 3/2001 |

*Primary Examiner* — Philip C Tucker
*Assistant Examiner* — Brian R Slawski
(74) *Attorney, Agent, or Firm* — McCormick, Paulding & Huber LLP

(57) ABSTRACT

Microfluidic devices are provided for conducting fluid assays, for example biological assays, that have the ability to move fluids through multiple channels and pathways in a compact, efficient, and low cost manner. Discrete flow detection elements, preferably extremely short hollow flow elements, with length preferably less than 700 micron, preferably less than 500 micron, and internal diameter preferably of between about 50+/−25 micron, are provided with capture agent, and are inserted into microfluidic channels by tweezer or vacuum pick-and-place motions at fixed positions in which they are efficiently exposed to fluids for conducting assays. Close-field electrostatic attraction is employed to define the position of the elements and enable ready withdrawal of the placing instruments. The microfluidic devices feature flow elements, channels, valves, and on-board pumps that are low cost to fabricate accurately, are minimally invasive to the fluid path and when implemented for the purpose, can produce multiplex assays on a single portable assay cartridge (chip) that have low coefficients of variation. Novel methods of construction, assembly and use of these features are presented, including co-valent bonding of selected regions of faces of surface-activatable bondable materials, such as PDMS to PDMS and PDMS to glass, while contiguous portions of one flexible sheet completes and seals flow channels, fixes the position of inserted (Continued)

analyte-detection elements in the channels, especially short hollow flow elements through which sample and reagent flow, and other portions form flexible valve membranes and diaphragms of pumps. A repeated make-and-break-contact manufacturing protocol prevents such bonding to interfere with moving the integral valve diaphragm portions from their valve seats defined by the opposed sheet member, which the flexible sheet material engages. Preparation of two subassemblies, each having a backing of relatively rigid material, followed by their assembly face-to-face in a permanent bond is shown. Hollow detection flow elements are shown fixed in channels, that provide by-pass flow paths of at least 50% of the flow capacity through the elements; in preferred implementations, as much as 100% or more. Metallized polyester film is shown to have numerous configurations and advantages in non-permanently bonded constructions. A method of preparing detection elements for an assay comprises batch coating detection elements, or hollow flow elements by mixing and picking and placing the elements in flow channels of a microfluidic device, capturing the flow elements by bonding two opposed layers while sealing the flow channels.

20 Claims, 45 Drawing Sheets

Related U.S. Application Data continuation-in-part of application No. PCT/US2010/057860, filed on Nov. 23, 2010, said application No. 13/427,875 is a continuation-in-part of application No. PCT/US2011/029736, filed on Mar. 24, 2011, which is a continuation-in-part of application No. PCT/US2010/057860, filed on Nov. 23, 2010.

(60) Provisional application No. 61/465,688, filed on Mar. 22, 2011, provisional application No. 61/608,570, filed on Mar. 8, 2012, provisional application No. 61/263,572, filed on Nov. 23, 2009.

(51) Int. Cl.
| | | |
|---|---|---|
| B32B 37/00 | (2006.01) | |
| B32B 38/00 | (2006.01) | |
| B65C 3/26 | (2006.01) | |
| B32B 38/04 | (2006.01) | |
| B32B 27/00 | (2006.01) | |
| G01N 33/00 | (2006.01) | |
| G01N 15/06 | (2006.01) | |
| G01N 33/48 | (2006.01) | |
| B01L 3/00 | (2006.01) | |
| C12M 1/34 | (2006.01) | |
| C12M 3/00 | (2006.01) | |
| F15C 1/06 | (2006.01) | |
| G01N 21/05 | (2006.01) | |
| G01N 21/64 | (2006.01) | |
| G01N 33/543 | (2006.01) | |
| B32B 37/14 | (2006.01) | |
| B32B 37/18 | (2006.01) | |
| G01N 21/03 | (2006.01) | |

(52) U.S. Cl.
CPC ...... *B01L 3/502761* (2013.01); *B32B 37/142* (2013.01); *B32B 37/18* (2013.01); *B32B 38/0008* (2013.01); *G01N 21/05* (2013.01); *G01N 21/645* (2013.01); *G01N 33/54366* (2013.01); *G01N 33/54386* (2013.01); *B01L 2200/0689* (2013.01); *B01L 2200/12* (2013.01); *B01L 2200/16* (2013.01); *B01L 2300/087* (2013.01); *B01L 2300/0858* (2013.01); *B01L 2300/0887* (2013.01); *B01L 2300/12* (2013.01); *B01L 2300/123* (2013.01); *B01L 2300/16* (2013.01); *B01L 2300/168* (2013.01); *B01L 2400/0481* (2013.01); *B01L 2400/06* (2013.01); *B01L 2400/0633* (2013.01); *B01L 2400/0638* (2013.01); *B01L 2400/086* (2013.01); *B29C 66/026* (2013.01); *B29C 66/028* (2013.01); *B29C 66/5225* (2013.01); *B29C 66/52298* (2013.01); *B29C 66/712* (2013.01); *B32B 2535/00* (2013.01); *G01N 2021/0346* (2013.01); *G01N 2021/058* (2013.01); *Y10T 29/494* (2015.01)

(58) Field of Classification Search
CPC ............ B29C 66/5225; B29C 66/5229; B29C 66/52298; B29C 66/71; B29C 66/712; B01L 3/502707; B01L 5/502715; B01L 2200/0887; B01L 2200/12; B01L 2300/0689; B01L 2300/0816; B01L 2300/0887; G01N 21/05; G01N 2021/0346
USPC ... 156/60, 64, 153, 155, 156, 182, 242, 245, 156/247, 272.2, 272.6, 278, 285, 286, 156/287, 289, 290, 292, 293, 294, 297, 156/298; 422/68.1, 502, 503; 435/283.1, 435/287.1, 287.3, 287.9, 288.3, 288.4, 435/288.5; 137/833; 436/180
See application file for complete search history.

(56) References Cited

U.S. PATENT DOCUMENTS

| | | | |
|---|---|---|---|
| 6,405,608 | B1 | 6/2002 | Lindgren et al. |
| 6,695,369 | B2 | 2/2004 | Schmidt et al. |
| 7,708,944 | B1 | 5/2010 | Sadik et al. |
| 7,754,148 | B2 | 7/2010 | Yu et al. |
| 7,947,492 | B2 | 5/2011 | Niehaus |
| 8,999,131 | B2 | 4/2015 | Ikegami et al. |
| 9,180,453 | B2 | 11/2015 | Chiu et al. |
| 9,207,236 | B2 | 12/2015 | Cary |
| 9,644,623 | B2 | 5/2017 | Mathies et al. |
| 9,651,039 | B2 | 5/2017 | Mathies et al. |
| 2002/0094584 | A1* | 7/2002 | Shieh et al. |
| 2002/0180963 | A1 | 12/2002 | Chien |
| 2003/0044855 | A1 | 3/2003 | Anderson et al. |
| 2004/0072278 | A1 | 4/2004 | Chou et al. |
| 2004/0231986 | A1 | 11/2004 | Rossier |
| 2004/0263923 | A1* | 12/2004 | Moon et al. |
| 2004/0265181 | A1* | 12/2004 | Noda et al. |
| 2005/0106752 | A1* | 5/2005 | Yu et al. |
| 2006/0063271 | A1* | 3/2006 | Putnam et al. |
| 2006/0073035 | A1 | 4/2006 | Sundararajan |
| 2006/0234298 | A1 | 10/2006 | Chiu et al. |
| 2007/0061093 | A1 | 3/2007 | Angelescu et al. |
| 2007/0159627 | A1 | 7/2007 | Johnson |
| 2008/0079873 | A1 | 4/2008 | Utsumi et al. |
| 2008/0280285 | A1 | 11/2008 | Chen et al. |
| 2010/0068723 | A1 | 3/2010 | Jovanovich et al. |
| 2010/0304494 | A1 | 12/2010 | Tokhtuev et al. |
| 2011/0120868 | A1 | 5/2011 | Lindsay et al. |
| 2011/0126911 | A1 | 6/2011 | Kobrin et al. |
| 2011/0206557 | A1 | 8/2011 | Phan et al. |
| 2011/0306120 | A1 | 12/2011 | Nicholls et al. |
| 2012/0070833 | A1 | 3/2012 | Wang |
| 2013/0089876 | A1 | 4/2013 | Sadik et al. |
| 2013/0200549 | A1 | 8/2013 | Felts et al. |
| 2013/0323737 | A1 | 12/2013 | Zenhausem et al. |

* cited by examiner

Mylar Film with Reflective Coating

Closed Valve

Open Valve

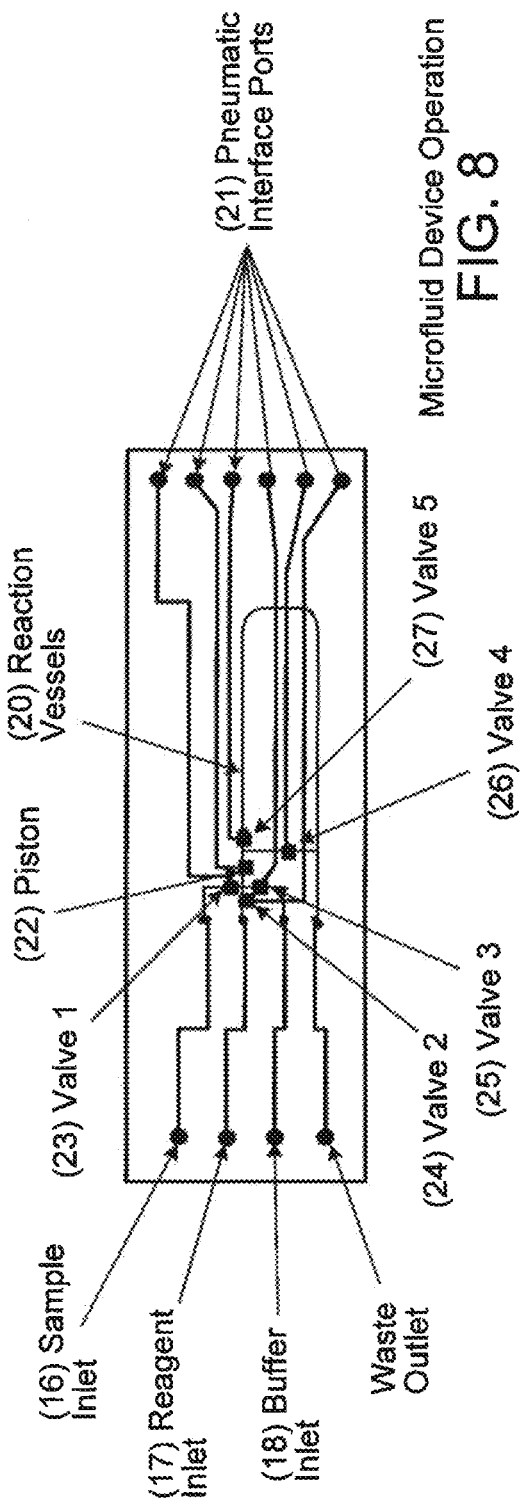
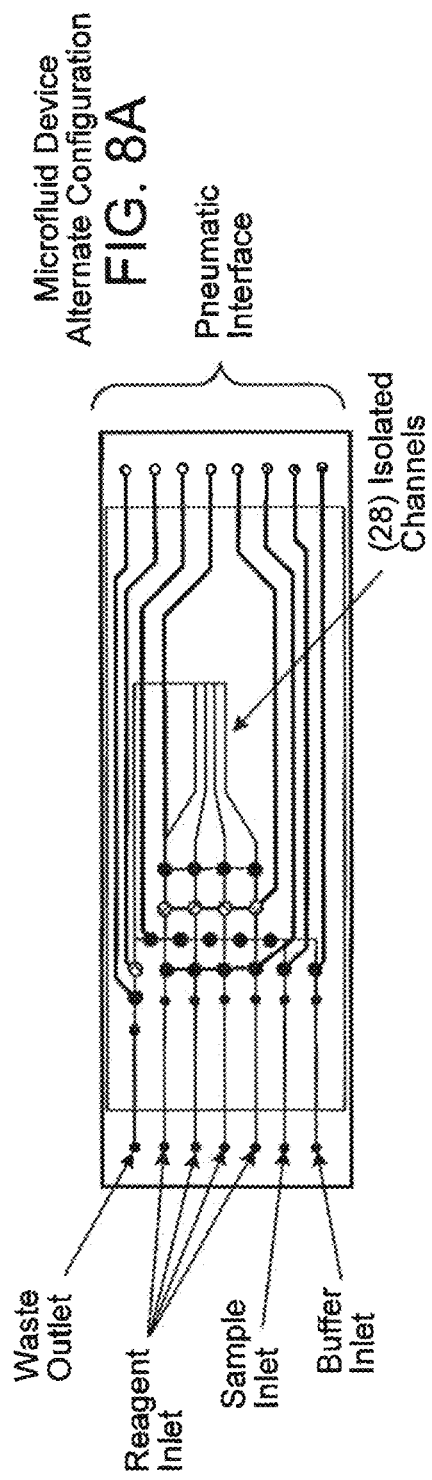

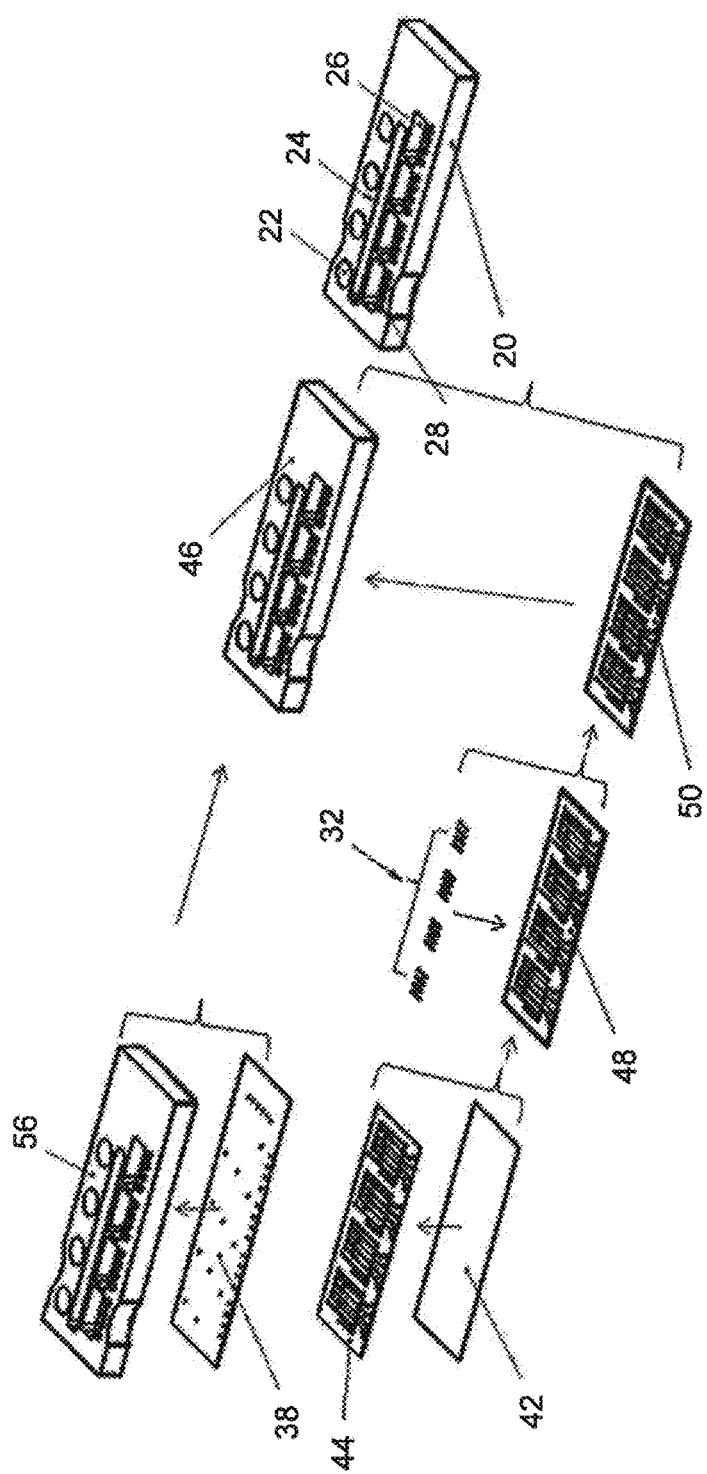

50

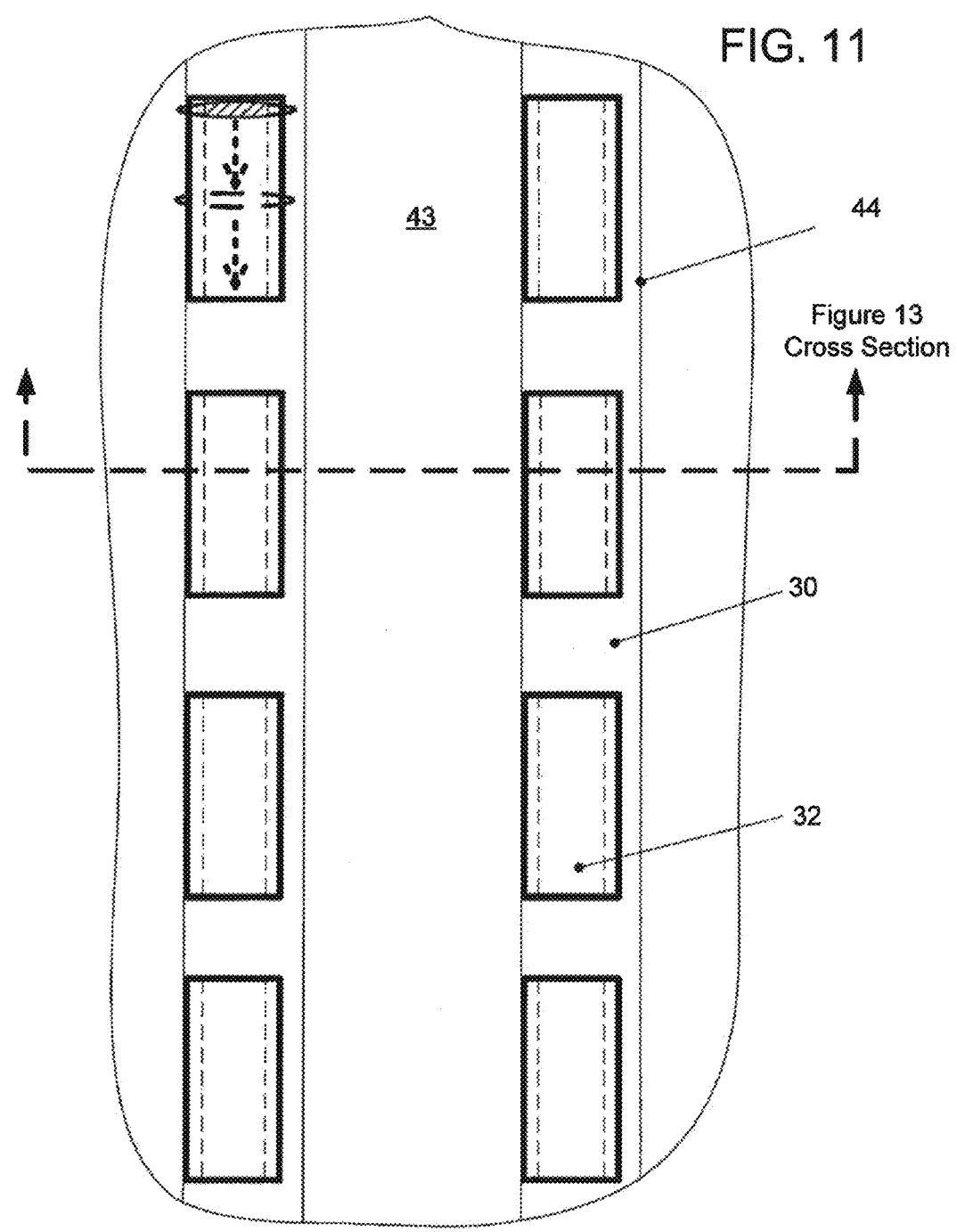

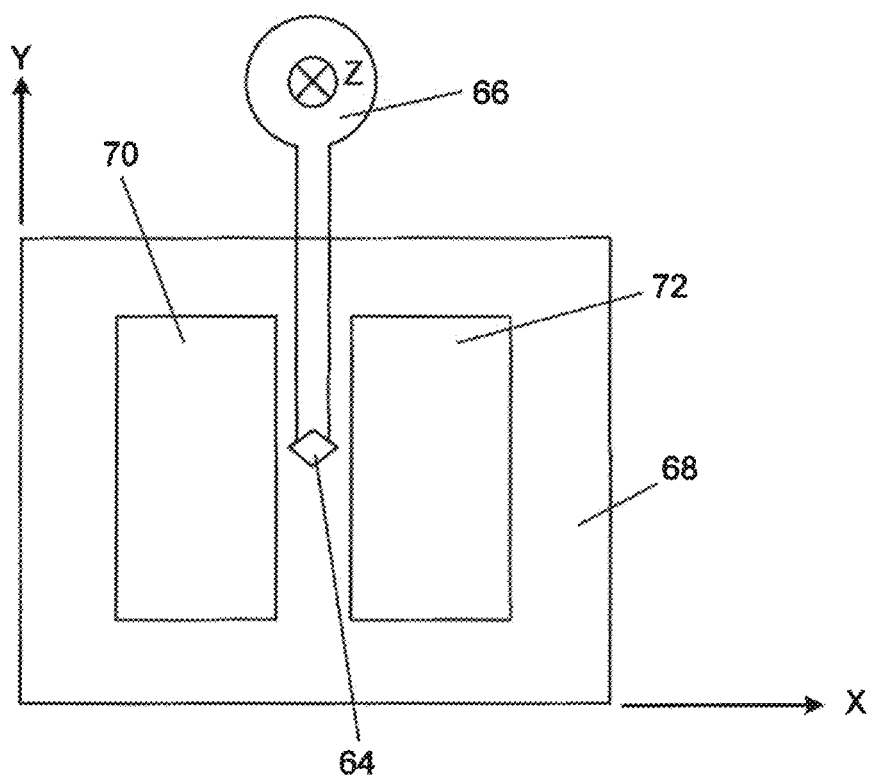

Pick & Place – Front View

MICROFLUIDIC DEVICES AND METHODS OF MANUFACTURE AND USE

CROSS-REFERENCE TO RELATED APPLICATIONS

This application is a divisional application of U.S. patent application Ser. No. 13/427,875 filed Mar. 22, 2012, now U.S. Pat. No. 9,216,412 B2, which claims priority to U.S. Application Ser. No. 61/465,688, filed on Mar. 22, 2011 and Ser. No. 61/608,570 filed Mar. 8, 2012, each of which is hereby incorporated entirely by reference to the extent permitted by applicable law, and U.S. patent application Ser. No. 13/427,875 filed Mar. 22, 2012, now U.S. Pat. No. 9,216,412 B2 is a Continuation-in-Part of PCT/US2010/057860 filed Nov. 23, 2010, which claims the benefit of U.S. Provisional Application 61/263,572 filed Nov. 23, 2009, and U.S. patent application Ser. No. 13/427,875 filed Mar. 22, 2012, now U.S. Pat. No. 9,216,412 B2 is a Continuation-in-Part of PCT/US2011/029736 filed Mar. 24, 2011, which is a Continuation-in-Part of PCT/US2010/057860 filed Nov. 23, 2010, which claims the benefit of U.S. Provisional Application 61/263,572 filed Nov. 23, 2009.

TECHNICAL FIELD

This invention relates to fluid assays, for instance biological assays, and to microcassettes or "chips" for conducting multiplex assays.

BACKGROUND

Despite a great amount of creative attempts to fabricate multiplex assay cassettes, for instance for protein assays with body fluid samples, the cost of manufacture remains high and the devices lack the desired coefficients of variation of substantially less than 10 to qualify them as practical quantification devices, to replace common blood tests, but with greater cost-effectiveness, as long has been foreseen as the future of research activities and personal medicine. There are many other assays to which the advantages of low cost, practical multiplex assay cassettes would be of great advantage.

SUMMARY

Microfluidic devices are provided for conducting fluid assays, for example biological assays, that have the ability to move fluids through multiple channels and pathways in a compact, efficient, and low cost manner. Discrete flow detection elements, preferably extremely short hollow flow elements, with length preferably less than 700 micron, preferably less than 500 micron, and internal diameter preferably of between about 50+/−25 micron, are provided with capture agent, and are inserted into microfluidic channels by tweezer or vacuum pick-and-place motions at fixed positions in which they are efficiently exposed to fluids for conducting assays. Close-field electrostatic attraction is employed to define the position of the elements and enable ready withdrawal of the placing instruments. The microfluidic devices feature flow elements, channels, valves, and on-board pumps that are low cost to fabricate accurately, are minimally invasive to the fluid path and when implemented for the purpose, can produce multiplex assays on a single portable assay cartridge (chip) that have low coefficients of variation. Novel methods of construction, assembly and use of these features are presented, including co-valent bonding of selected regions of faces of surface-activatable bondable materials, such as PDMS to PDMS and PDMS to glass, while contiguous portions of one flexible sheet completes and seals flow channels, fixes the position of inserted analyte-detection elements in the channels, especially short hollow flow elements through which sample and reagent flow, and other portions form flexible valve membranes and diaphragms of pumps. A repeated make-and-break-contact manufacturing protocol prevents such bonding to interfere with moving the integral valve diaphragm portions from their valve seats defined by the opposed sheet member, which the flexible sheet material engages. Preparation of two subassemblies, each having a backing of relatively rigid material, followed by their assembly face-to-face in a permanent bond is shown. Hollow detection flow elements are shown fixed in channels, that provide by-pass flow paths of at least 50% of the flow capacity through the elements; in preferred implementations, as much as 100% or more. Metallized polyester film is shown to have numerous configurations and advantages in non-permanently bonded constructions.

In one aspect there is featured a microfluidic device for conducting a fluid assay, for example a biological assay, having a flow channel in which is inserted at least one discrete flow detection element (preferably an extremely short hollow flow element with length less than about 700 micron, preferably less than about 500 micron, and internal diameter of between about 75+/−50 micron, preferably in many instances 50+/−25 micron, in fixed position), that is provided with capture agent, the flow element being positioned for exposure to fluid flows within the device for conducting an assay. Additional aspects of this feature include one or more of the following features, as indicated by the claims The device in which the detection element is inserted into its microfluidic channel by pick-and-place motion.

The device in which the detection element comprises a short hollow flow element of length less than 700 micron, preferably less than approximately 500 micron, having oppositely directed planar end surfaces and a cylindrical outer surface extending between those end surfaces, and preferably so located in the flow channel to permit flow through the element, and by-pass flow of at least equal volume along the outside of the fixed element.

The device in which the pick and place motion is effected by automated tweezer fingers engaging oppositely directed portions of the flow element, preferably oppositely directed parallel planar surfaces.

The device in which the pick and place motion is effected by automated vacuum pick up.

The device in which the vacuum pickup device engages an outer cylindrical surface of the flow element.

The device in which flow channel closure, flexible diaphragm for fluid-actuated valve or on-board pump diaphragm, preferably all three, are provided by a respective portion of a flexible sheet that in other places of substantial area is joined by bonding to an opposed surface.

The device in which the flexible diaphragm sheet is comprised of a non-elastomeric, non-air-permeable flexible sheet, preferably a polyester film.

The device in which the flexible sheet is metallized, preferably with aluminum, to reflect incident or fluorescent light with respect to detector optics.

The device in which the detector is of epi-fluorescence type, and the metallized film is positioned to reflect incident excitation light and fluorescing light associated with the presence of a desired analyte.

The device in which the flexible non-air-permeable sheet is bonded face to face with an elastomeric film exposed for contact with the fluid sample.

The device in which the flexible sheet consists of elastomer, preferably PDMS.

The device in which the device is constructed to conduct multiplex assays on a single portable assay cartridge (chip).

The device in which at least some parts of the device are joined by co-valent bonding of activated surfaces of bondable material, a contiguous portion of the same sheet fixing the position of a said detection element in its flow channel.

The device in which at least some parts of the device are joined by co-valent bonding of activated surfaces of bondable material, a contiguous portion of the same sheet forming a flexible pump diaphragm.

The device in which at least some parts of the device are joined by co-valent bonding of activated surfaces of bondable material, a contiguous portion of the same sheet forming a flexible valve diaphragm.

The device in which the flexible valve diaphragm portion engages a valve seat originally formed of surface-activated bondable material that has been subjected to a series of make- and break contacts that interrupt covalent bonding of the valve diaphragm portion with its opposed seat.

The device in which at least some parts of the device are joined by co-valent bonding of activated surfaces of bondable material, and respective contiguous portions of the same sheet seal an open side of a flow channel, fix the position of a said detection element in its flow channel, form a flexible pump diaphragm or form a flexible valve diaphragm, preferably respective portions of the sheet performing all of these functions.

The device in which parts are permanently secured by co-valent bonding of selected regions of faces of surface-activated bondable materials.

The device in which the form of activation is oxidation.

The device in which at least one of the parts comprises surface-activatable elastomer.

The device in which the elastomer is PDMS.

The device in which the bond is formed by opposed surfaces of surface-activated PDMS.

The device in which the bond is formed by one opposed surface of surface-activated PDMS and the other surface is surface-activated glass or polymer other than PDMS.

The device formed by preparation of two subassemblies, each having a backing of relatively rigid material and an oppositely directed face suitable for bonding to a mating face of the other subassembly, followed by bonding the assemblies face-to-face.

The device in which the bonding creates a permanent bond, preferably, in the case of like surfaces, such as of PDMS, a bond of surface-activated surfaces in which the original structure of mating surfaces is substantially eliminated by molecular diffusion.

The device in which the bond is separable such as for enabling re-use of the device.

The device in which the bonding is substantially formed by electrostatic attraction.

The device in which the detection element comprises a cylindrical, hollow flow element of length no greater than 700 micron, preferably less than about 500 micron, most preferably about 200 micron and internal diameter of approximately 75+/−50 micron, preferably in many instances 50 micron+/−25 micron, the element being substantially uniformly coated on its inner surface with capture agent for a selected fluid assay.

The device in which the capture agent is antibody for conducting ELISA.

The device in which capture agent is substantially absent from all outer surfaces of the element, and the detection element is sized, relative to the channel in which it is inserted, to define a substantial flow path through the element and a substantial by-pass flow path along the exterior of the element.

The device in which the detection element is of depth greater than the depth of an open channel in which it is inserted, and a capturing layer closes and seals the channel, the capturing layer being elastically deformed by its contact with the flow element thereby and applying forces thereto that fix the location of the element in the channel.

The device in which the capturing layer is co-valently bonded to the substance defining the open channel.

The device in which the capturing layer and the substance both comprise PDMS.

The device in which a portion of the capturing layer forms a valve diaphragm adapted to engage a seat formed by the opposed material, the portion having been subjected to repeated make-and-break-seat-contact manufacturing protocol that interferes with co-valent bonding of the mating valve surfaces.

The device is constructed to perform ELISA biological assay.

The device in which a series of between about 3 and 10 spaced-apart discrete flow elements of less than 700 micron length, preferably less than about 500 micron, are fixed in a given channel.

The device in which a fluorophor labels captured analyte, and the flow elements are exposed to a window transparent to outwardly proceeding fluorescent emission for detection.

The device window is transparent to exterior-generated stimulating light emission to enable epi-fluorescent detection.

In another aspect, a microfluidic device is provided for conducting a fluid assay, for example a biological assay, having a flow channel in which is inserted at least one discrete flow detection element that is provided with capture agent, the flow element being positioned for exposure to fluid flows within the device for conducting an assay, the device formed by preparation of two subassemblies, each having a backing of relatively rigid material and an oppositely directed face suitable for bonding to a mating face of the other subassembly, followed by bonding the assemblies face-to-face.

Preferred implementations have further features as indicated by the claims;

In the device the bond is breakable, such as an electrostatic bond, to enable detachment of the two subassemblies.

In the device the bond is permanent, formed by bonding together two surface-activated surfaces.

In the device the member defining one of the surfaces has portions that fix the position of a said detection element in its flow channel, form a flexible pump diaphragm or form a flexible valve diaphragm, preferably respective portions of the sheet performing all of these functions.

In the device a flexible valve diaphragm portion engages a valve seat originally formed of surface-activated bondable material that has been subjected to a series of make- and break contacts that interrupt covalent bonding of the valve diaphragm portion with its opposed seat.

In the device the mating surfaces are both of PDMS.

In another aspect a microfluidic device is provided for conducting a fluid assay, for example a biological assay, having a flow channel in which is inserted at least one discrete flow detection element comprising an extremely short hollow flow element with length less than about 700 micron, preferably less than about 500 micron, and internal diameter of between about 75+/−50 micron, preferably in many instances 50+/−25 micron, in fixed position, that is provided with capture agent, the flow element being positioned for exposure to fluid flows within the device for conducting an assay the flow element being secured in fixed position by an overlaying layer of material that is surface activated and bonded by molecular bonding to an opposing member in adjacent regions.

In another aspect a microfluidic device is provided conducting a fluid assay, for example a biological assay, having a flow channel in which is inserted at least one discrete flow detection element (preferably an extremely short hollow flow element with length less than about 700 micron, preferably less than about 500 micron, and internal diameter of between about 75+/−50 micron, preferably in many instances 50+/−25 micron, in fixed position), that is provided with capture agent only on its interior, the flow element being positioned for exposure to fluid flows within the device for conducting an assay, the flow channel being of rectangular cross-section, the exterior of the element being of cylindrical cross-section, and by-pass flow paths are defined along the exterior of the element.

In another aspect, a discrete detection element is provided in the form of an extremely short hollow flow element with length less than about 700 micron, preferably less than about 500 micron, and internal diameter of between about 75+/−50 micron, preferably in many instances 50+/−25 micron, the flow element provided with capture agent, the flow element being constructed to be fixed in position for exposure to fluid flows within a device for conducting an assay. In some implementations the capture agent resides only on the interior surface of the element.

In another aspect, a discrete detection element is provided in the form of a hollow flow element carrying on its interior surface, but not its exterior surface, an assay capture agent, the element fixed in position in a fluid channel in manner that provides at least about 50% by-pass flow capacity relative to the flow capacity through the element. In certain implementations the by-pass flow capacity is about 75% or more, relative to the flow capacity through the element, while in others the by-pass flow capacity is about 100% or more, relative to the flow capacity through the element.

Another feature is a method of manufacturing the device or element of each of the above.

Another feature is a method of use of the device or element of any of the above.

Another feature is a method of preparing detection elements for an assay comprising batch coating the detection elements, preferably hollow flow elements by mixing in solution, and drying, and thereafter picking and placing the elements in flow channels of a microfluidic device, and preferably capturing the flow elements by bonding two opposed layers that capture the elements while sealing the flow channels.

Other important features comprise the disclosed methods of manufacturing each of the foregoing devices.

Other important features comprise the disclosed methods of use of any of each of the foregoing devices.

The details of one or more embodiments of each invention are set forth in the accompanying drawings and the description below. Other features, objects, and advantages of the invention will be apparent from the description and drawings, and from the claims.

DESCRIPTION OF DRAWINGS

FIG. 8—Microfluidic Device Operation;
FIG. 8A—Microfluidic Device Alternate Configuration;
FIG. 9—A schematic diagram in perspective of assembly steps for another microfluidic assay device;
FIG. 10A—A perspective view of a fluidic channel of FIGS. 9 and 10;
FIG. 10B—A magnified view of a portion of FIG. 10A showing flow channels, hollow flow elements, valve seats and pump chambers;
FIG. 11—A greatly magnified plan view of a portion of the channel structure, showing two channels, with four hollow flow elements disposed in each;
FIG. 18B—A magnified view of a portion of FIG. 18A;
FIG. 18C—A perspective view of the completed assembly, viewed from above;
FIG. 18D—A perspective view of the completed assembly, viewed from below.

FIG. 21—A diagram of a pick-and-place instrument positioned above an X,Y translation table, a delivery plate for discrete, extremely small hollow flow elements and a receiving channel of multiplex micro-fluidic assay devices of the preceding Figures;

Like reference symbols in the various drawings indicate like elements.

DETAILED DESCRIPTION

It is the purpose of the inventions is to deliver a microfluidic device for conducting biological assays, with the ability to move fluids through multiple channels and pathways in a compact, efficient, and low cost manner.

In most implementations the assay device will be comprised of multiple substrates stacked together to create three primary layers; (a) Pneumatic/Fluidic Interface Layer, (b) Channel Closure Layer, and (c) Fluidic/Reaction Vessel Layer. Further, the device will contain microfluidic valves and pistons for driving, controlling, and manipulating the fluid flow. The following description, referring to FIGS. 1A, 1B, 2A, 2B, 2C, 3A, 3B, 4A, 4B, 4C, 5, 6A, 6B, 7A, 7B, 7C, 8, and 8A, covers one particular configuration of the microfluidic device, in terms of the fluidic/pneumatic channel architecture, placement of valves, pistons, and inlet ports, however the scope of this invention is not intended to be limited to this particular configuration, and is intended to include other configurations, both known now, for instance the later embodiment presented, and later developed in the future.

Figure 1A:
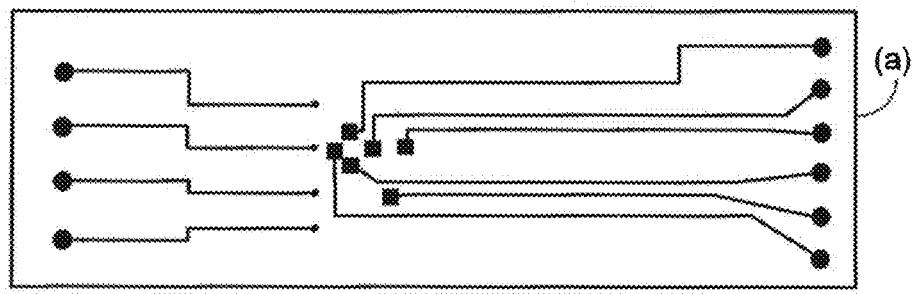
FIGS. 1A and 1B—Pneumatic/Fluidic Interface Layer (a)
Figure 1B:
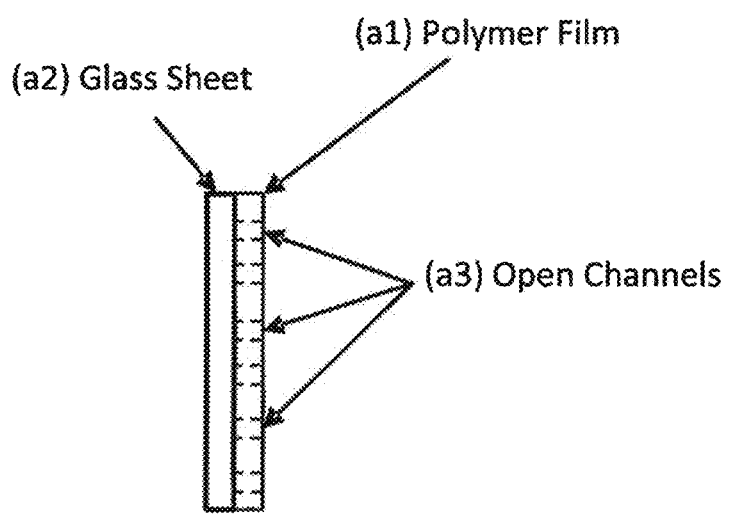

FIGS. 1A and 1B—Pneumatic/Fluidic Interface Layer (a)

FIGS. 1A and 1B depict the Pneumatic/Fluidic Layer (a) which is comprised of a glass sheet, such as a microscope slide (a2), upon which a flexible polymer film (a1), approximately 150 μm thick, with through cut channels is attached, such that they form open channels or trenches (a3), which are closed on one side by the glass sheet (a2) and open on the other.

Figure 2A:
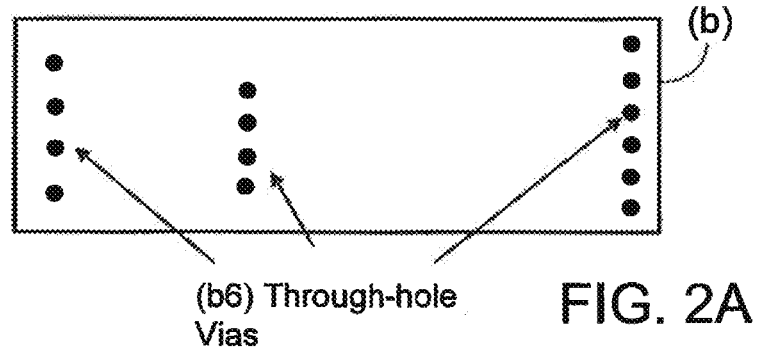
FIGS. 2A, 2B, and 2C—Channel Closure Layer (b)
Figure 2B:
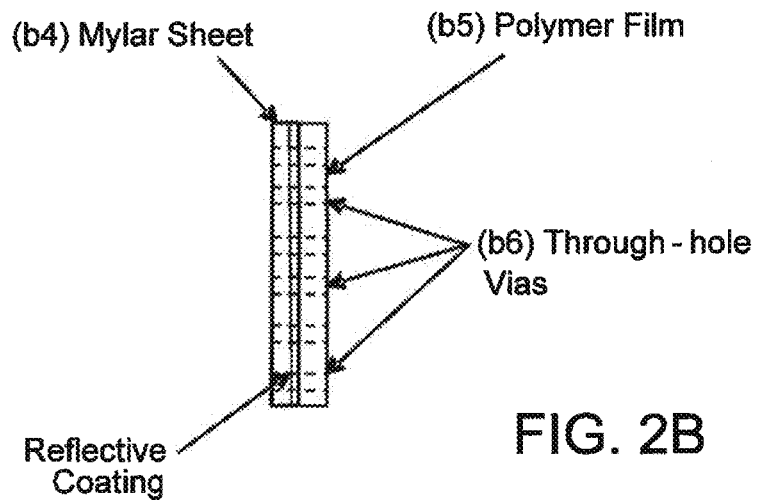
Figure 2C:
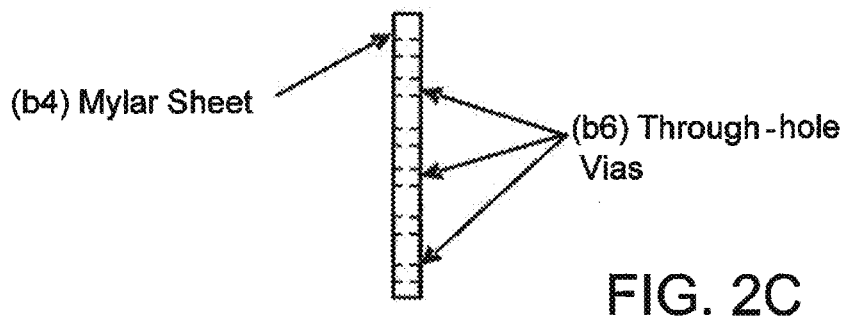

FIGS. 2A, 2B, and 2C—Channel Closure Layer (b)

FIGS. 2A, 2B, and 2C depict the Channel Closure Layer (b) which is formed by attaching a mylar sheet (b4), approximately 12 μm thick, with precut, through-hole vias (b6) and a reflective coating such as aluminum, to a sheet of flexible polymer (b5), approximately 150 μm thick with corresponding precut vias (b6). Note: in alternate embodiments, for example as shown in FIGS. 2C and 4C, it is envisioned that the Channel Closure Layer (b) could be comprised of just the mylar sheet (b4), with or without the reflective coating, and no flexible polymer sheet. The Channel Closure Layer (b) is permanently bonded to the Pneumatic/Fluidic Layer (a), closing off the top of the channels in the Pneumatic/Fluidic Layer (a) and thereby forming closed channels. In addition to serving as a top closure for the channels in the Pneumatic/Fluidic Layer (a), the Channel Closure Layer (b) provides the following functionality:

Through hole vias (b6) to allow the passage of fluids and pneumatics from the Pneumatic/Fluidic Layer (a) to the Fluidic/Reaction Vessel Layer (c).

The Channel Closure Layer (b) is constructed of compliant materials that flex as part of valve and pump actuation.

The polyester film (Mylar™ from DuPont) (b4) provides a gas impermeable layer which is a necessary component of the pumps and pistons described later in this document.

Figure 5:
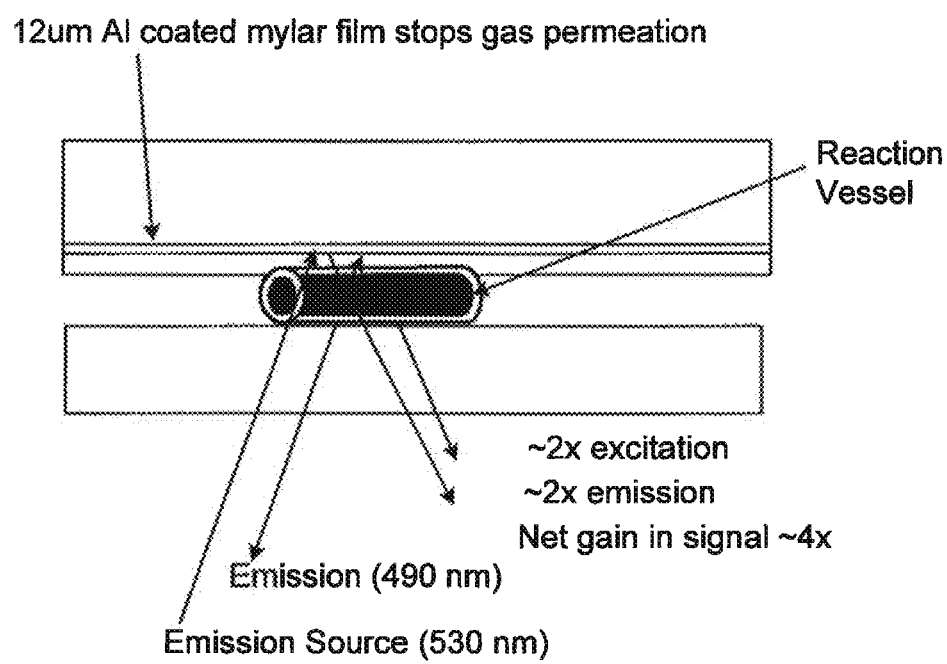
FIG. 5—Mylar Film with Reflective Coating.

The reflective coating on the mylar layer (b4) reflects the excitation energy before it reaches the mylar, thereby preventing auto-fluorescence (see FIG. 5)

The reflective coating reflects the excitation energy back onto the Reaction Vessels which results in a 2 fold multiplication of the incident fluorescence, and a 2 fold increase in the emitted fluorescence thereby enhancing the capture of emitted radiation by nearly 2 fold. This results in a nearly four-fold overall increase of un-reflected fluorescence signal relative to the reflected signal, thereby producing a nearly four-fold increase in detection signal.

Figure 3A:
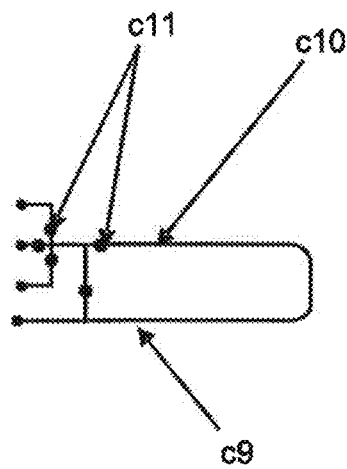
FIGS. 3A and 3B—Fluidic/Reaction Vessel Layer (c)
Figure 3B:
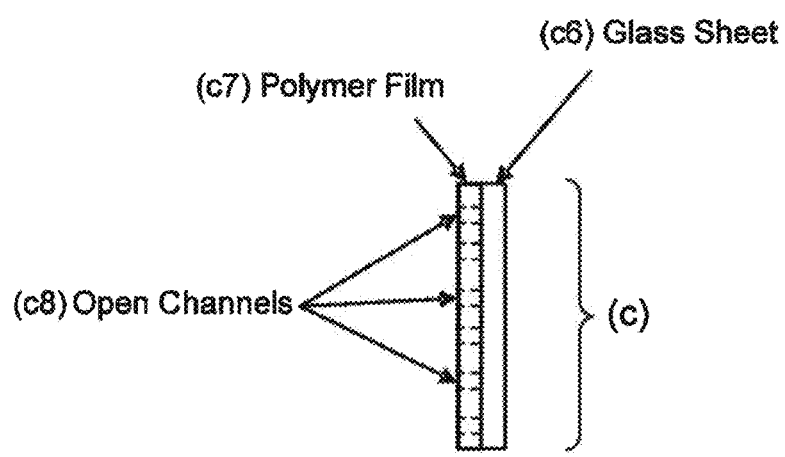

FIGS. 3A and 3B—Fluidic/Reaction Vessel Layer (c)

FIGS. 3A and 3B depict the Fluidic/Reaction Vessel Layer (c) which is comprised of a thin glass sheet (c6), such as a 200 μm thick glass cover slip, upon which a flexible polymer film (c7), approximately 150 μm thick, with through cut channels is attached, such that they form open channels or trenches (c8), which are closed on one side by the glass sheet (c6) and open on the other. These channels provide a path for fluids (c9), channel(s) to house reaction vessels (c10), and provide features for the on-board valves and pistons (c11). Reaction Vessels are inserted into the Fluidic/Reaction Vessel Layer (c) and it is then attached to the Channel Closure Layer (b) (side not occupied by the Pneumatic/Fluidic Layer) thereby closing off the top of the channels in the Fluidic/Reaction Vessel Layer (c) and forming closed channels as depicted in FIG. 4.

Figure 4A:
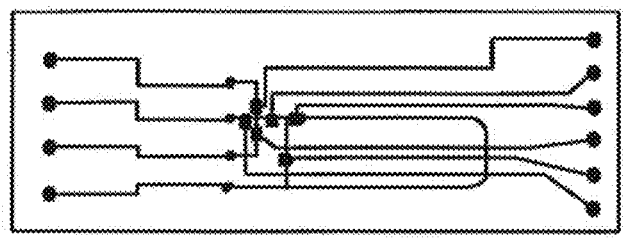
FIGS. 4A and 4B—Fully Assembled Microfluidic Device.
Figure 4B:
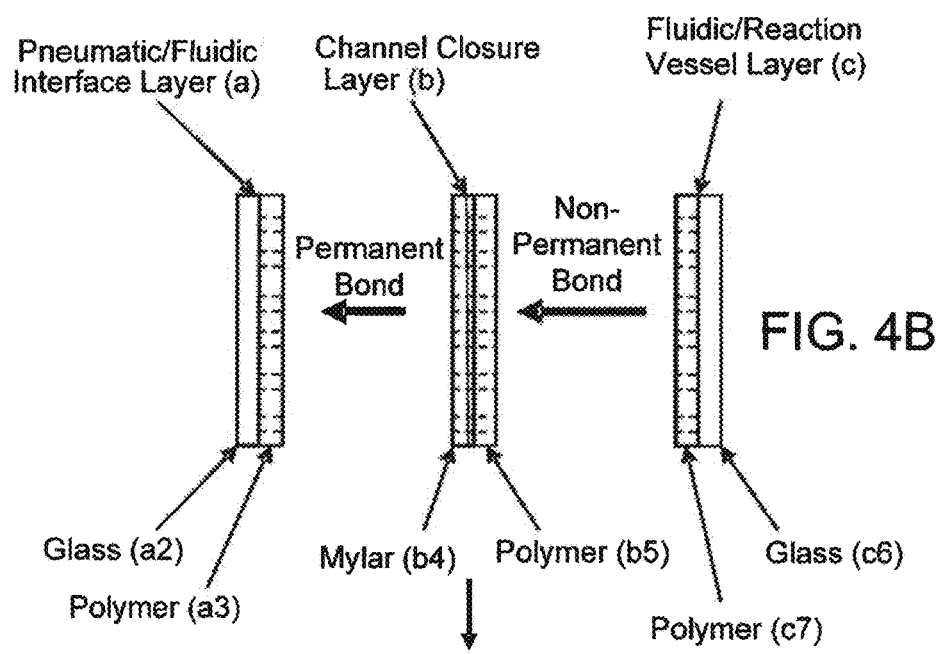
Figure 4C:
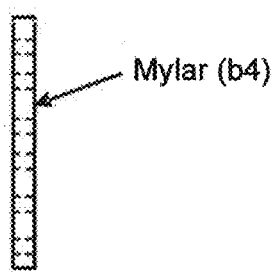
FIG. 4C—Alternate embodiment.

FIGS. 4A, 4B, and 4C—Fully Assembled Microfluidic Device

FIG. 5—Mylar Film with Reflective Coating

This microfluidic device contains on-board, pneumatically actuated, pistons and valves for the purpose of driving, controlling, and manipulating the fluid flow. This will include introducing and metering the flow of biological samples, reagents, diluents, and wash buffers as well as controlling the flow rates and incubation times for assays being conducted in the reaction vessels.

Figure 6A:
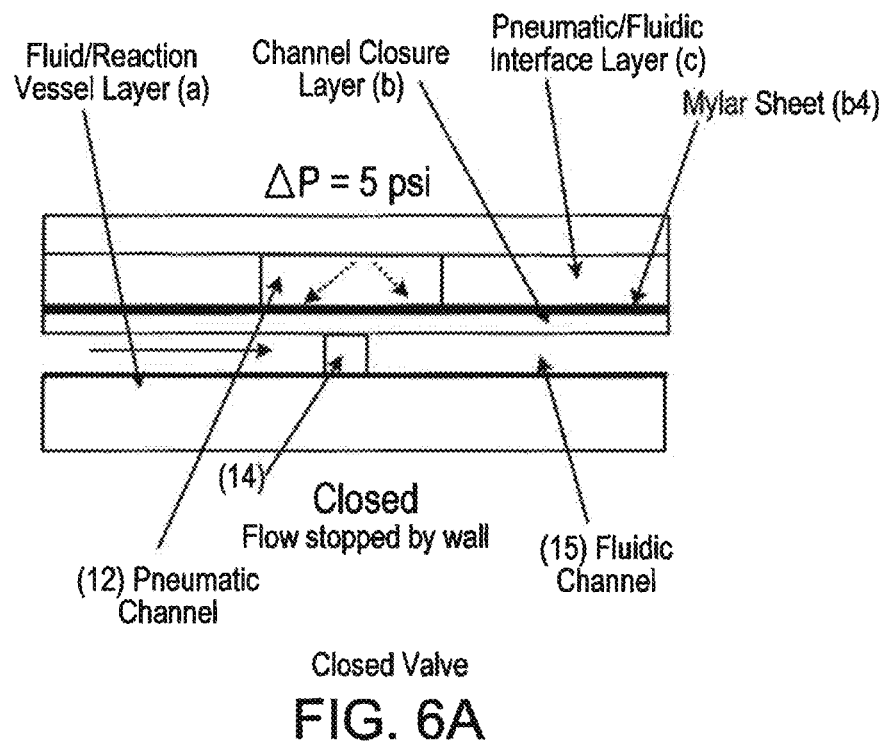
FIGS. 6A and 6B—Microfluidic Valve.
Figure 6B:
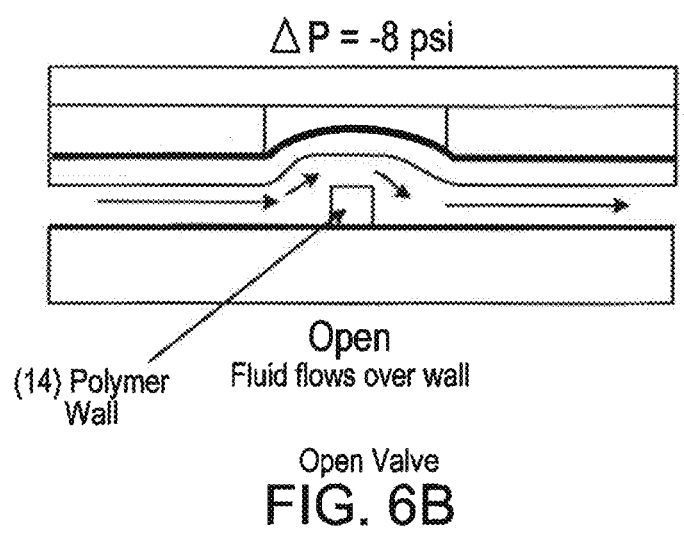

FIGS. 6A and 6B—Microfluidic Valve

The valves are actuated by applying negative pressure to the Pneumatic Channels (12) contained in the Pneumatic/Fluidic Layer (c), thereby flexing the compliant Channel Closure Layer (b) and lifting it off of the Polymer Wall (14), allowing fluid to flow through (see FIG. 6B). In order to maintain a tight seal when the negative pressure is released and the compliant layer is allowed to relax, it is necessary to apply positive pressure (see FIG. 6A). The compliant Channel Closure Layer (b) contains a mylar sheet (b4) which is gas impermeable thereby preventing the infiltration of gasses into the fluidic channel (15).

Figure 7A:
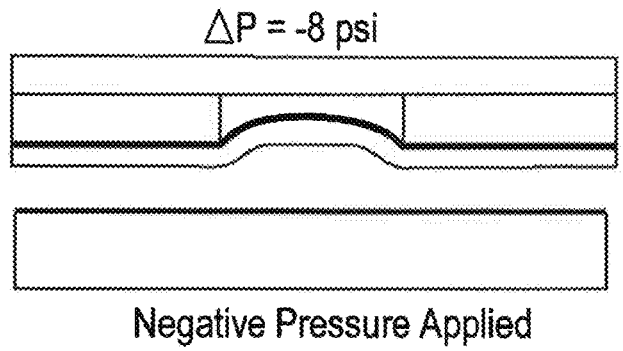
FIGS. 7A, 7B, and 7C—Microfluidic Piston.
Figure 7B:
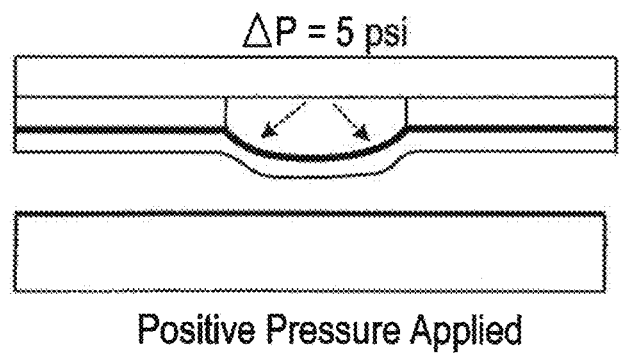
Figure 7C:
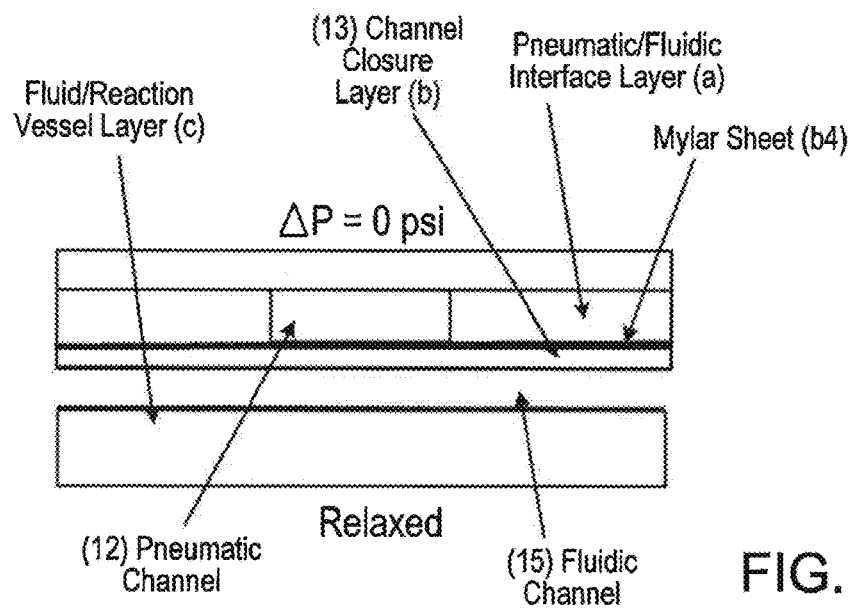

FIGS. 7A and 7B—Microfluidic Piston

The pistons are actuated by applying negative (FIG. 7A) and positive (FIG. 7B) pressure to the Pneumatic Channels (12) contained in the Pneumatic/Fluidic Interface Layer (a), thereby flexing the compliant Channel Closure Layer (b) and creating positive and negative pressure within the fluidic channel (15). An arrangement consisting of one microfluidic piston with a microfluidic valve on either side can be actuated in a sequence that will drive fluids in two directions. The compliant Channel Closure Layer contains a mylar sheet (b4) which is gas impermeable thereby preventing the infiltration of gasses into the fluidic channel (15).

FIG. 8—Microfluidic Device Operation

By way of example, following is a description of the operation of one possible configuration of the microfluidic device. This is shown by way of example, and the invention is not intended to be limited to this particular configuration listed below, and is intended to include other configurations, both known now and later developed in the future. Configurations with a plurality sample inlets, reagent wells, buffers, as well as plurality of isolated channels (28) for reaction vessels are envisioned, for example FIG. 8A depicts a microfluidic device with 4 reagent wells and 4 isolated channels (28) for reaction vessels.

1. Sample is added to the sample inlet (16), Reagent is added to reagent inlet (17), and buffer is added to buffer inlet (18).

2. Valve 1 (23) is opened and closed in conjunction with Valve 5 (27) and the piston (22) to draw the sample (16) into the reaction vessel (20).

3. Valves 1, 2, 3, and 4 are closed, and Valve 5 (27) and the piston (22) are opened and closed to drive the Sample (16) into the waste outlet. Note this process id repeated for the Reagent (step 4) and the Buffer (step 5)

4. Valve 2 (24) is opened and closed in conjunction with Valve 5 (27) and the piston (22) to draw the Reagent (17) into the reaction vessel (20).

5. Valve 3 (25) is opened and closed in conjunction with Valve 5 (27) and the piston (22) to draw the Buffer (18) into the reaction vessel (20).

FIGS. 1B, 2B, and 5—Shallow channels (trenches) into which are Inserted correspondingly small Reaction Vessels.

The Fluidic/Reaction Vessel Layer (a) is shown defined by a base of rigid material, in the example, a glass microscope slide and an attached polymeric layer, there being open channels (a3) formed as slots cut in the polymeric layer. The depth of channel (a3) is thus defined by the thickness of the polymer film attached to the base. Spanning that depth is an inserted reaction vessel, as shown in FIG. 5, in the form of a short hollow flow tube. In the example, the glass base is 200 µM thick, the polymeric film is approximately 150 µM thick, and as shown in FIG. 5, the vessel is of discrete short length, a few multiples of its outer diameter. The channel is closed about the hollow flow element by channel closure layer (b), with a non-permanent bond.

FIGS. 2B and 2C, 4B and 5—Polyester film (Mylar, DuPont's™) as Channel Closure Layer (b)—Advantages Three different combinations of materials provide respective advantages. The simplest construction is to use, thin polyester (Mylar™) film, by itself as a flexible membrane instead of a flexible elastomeric membrane as is common in microfluidic devices. Polyester film has the great advantage of low gas permeability. One particular problem with an elastomeric membrane is that to actuate the valves and the pistons a positive pressure is applied on the air side of the membrane to close the valves and a vacuum pressure is applied to open the valves. When valves are held closed using positive pressure, gas permeability of elastomeric membranes allows whatever gas is on the pressure side of the membrane to permeate through the membrane and that can lead to detrimental gas bubble formation in the fluidic channel. Bubble formation in fluidic channels is a particular problem if, as does occur, seed bubbles already exist on the fluidic side. Though if the fluidic channel in the valve region is completely filled and free of bubbles, gas permeation is very low and not a problem to the assay. However, in the event that there are pre-existing bubbles on that valve seat, then gas permeation from the gas pressure side to the fluidic side will occur and cause the small bubbles already there to in size, and affect the accuracy of the assay. Bubbles can disturb the uniformity of the capture when the fluid is exposed to capture agent. They can change the flow dynamics, i.e. cause the fluid to flow around the bubble and change binding kinetics and so forth in that area. In general, they are unwanted because they are perceived to create variability in assay processes.

It has been realized to be an advantage, especially in high pressure systems, to prevent the generation of gas bubbles from the actuation of the valves and the pistons by using a non-elastomeric, gas impermeable membrane, an excellent choice being polyester (Mylar™). To bond the polyester film to the channel-defining layer, for instance PDMs, chemical pretreatment and exposure to oxidizing plasma enables bonds to be formed between the layers to close the channels during the assay.

Polyester film (Mylar™) is well known to be orders of magnitude stiffer than elastomers such as PDMS, but, it is realized to be possible to increase the cross-sectional area, the footprint of the valve and the piston, to get the same motion of actuation that one gets from a very flexible membrane such as an elastomer. There are many situations in which density of networks is not required to be high, so that an enlarged actuation region of membrane can be accommodated.

There are of course other situations in which it is highly desirable to increase the density of elements in a network so that one can achieve more functionality in a smaller footprint. Implementations described below achieve that, i.e. the capability to assays, run more a variety of assays, more samples, more analytes, more of everything in a smaller footprint. Nevertheless, the use of the polyester (Mylar™ film is considered a significant step forward for certain assays.)

In many instances it often has been desirable to drive fluid flow in a microfluidic device with high fluid pressures, using an external pump such as a syringe pump, or a peristaltic pump. This has been necessary when high flow rates are required and in other instances when it is necessary to produce high flow rates through very small channels which require high external pressures. Valves are of course needed in such devices. In most cases when it is desirable to hold off flow through a valve with a very high back pressure on it, it is necessary to have a very high pneumatic actuation pressure to keep that valve seat closed. We realize this high pressure applied to the membrane promotes detrimental diffusion of air through the membrane, can be avoided by provision of non-elastomer, gas impermeable membrane, e.g. polyester film, to yield lower coefficients of variation of the assay.

There is a property of polyester film that may be thought to prevent its use, that of high auto fluorescence, especially in the presence of green laser light. But there are other detection techniques, e.g. chemiluminescence, electrochemiluminescence and photochromic processes, which are often employed for immunoassays, in which auto-fluorescence does not present a problem.

There are other cases in which it is desired to employ epifluorescence (light stimulated fluorescence emissions as the detection mode, in which autofluoescence of the membrane through which light must pass is a potential problem, but unique solutions presented here solve that problem.

As provided here, one solution to the problem is to use polyester film (Mylar™) with a reflective coating, e.g. an aluminum vapor coating on the side of the membrane facing the excitation source. The stimulating laser in an epifluorescent detection system thus is prevented from the auto fluorescence in the polyester, because light incident on the membrane is simply reflected by the reflective coating and does no reach the auto-fluorescent substance. In this case, as shown in FIG. 5, additional benefits accrue, in that one gets an increased signal capture both from the viewpoint that the excitation beam has opportunity to excite the fluorescent object of interest twice, once on its way through and once on its way back. The fluorescent emission is subject to double capture, i.e. the detector detects direct fluorescent emission and reflected fluorescent emission. So there is a signal benefit in using the reflective coating.

The third advantageous construction employing polyester film (Mylar™) is that shown in the FIGS. 4A, 4B, 4C, 5, 6A, 6B, 7A, 7B, and 7C above and related text, in which is avoided contact of the metallic surface with the sample and reagent fluids in the channel. It is not always desirable for any kind of metallized surface in a microfluidic channel to contact the fluids for fear of reactivity with the chemicals.

Also subjecting the metallized surface to wet conditions may detrimentally affect stability of the adherence of the metal to the polyester film (Mylar™). The hybrid membrane structure shown in FIGS. 4A, 4B, 4C, 5, 6A, 6B, 7A, 7B, and 7C, with an elastomeric layer bonded to the polyester film, and defining the surface exposed to the fluids solves this problem.

For the above implementations, whether the channels are formed in an elastomeric structure such as PDMS, or formed in an injection molded or embossed plastic part or in glass or etched in ceramic, is not of consequence regarding this feature. The business end of the valve is the flexible membrane. That is what would consists of one layer of non-elastomer, vapor impermeable film such as polyester (Mylar™) and one layer of elastomer such as PDMS or one layer of the polyester film, with aluminum on it or one layer of the polyester film with no reflective coating.

In this implementation, there is no externally driven flow with a syringe pump or a peristaltic pump. All flow is produced by onboard pistons and onboard valves formed by regions of a membrane that, in other regions, complete and seal the fluid channels. Any combination of states of those pistons and valves create flow in whatever direction needed, while venting substantially with atmospheric pressure on the liquid side of the device. With this construction, an elastomeric membrane, preferably PDMS, is employed.

The piston is constructed to be actuated in manner similar to the valves. On the pneumatic side of the membrane it uses both pressure and vacuum to create deflection of this flexible membrane. Pressure applied on the pneumatic side of the membrane, pushes the piston down into a cavity in the fluidic channel (the pump chamber), an action which displaces fluid and pushes fluid out of that cavity. The fluid will flow in the direction of lowest pressure. So if the fluidic channel is blocked on one side of the piston by a valve, then flow occurs in the other direction, towards a vented region.

The mechanism for flowing reagents and fluids within the microfluidic channels using pneumatic and vacuum actuated pistons, is referred to a peristaltic process. The piston is deflected either into or out of the fluidic chamber which, respectively, displaces fluid from the piston chamber on the fluidic side or draws fluid into the chamber. In the case where the piston is being actuated by vacuum, it is drawn up away from or out of the fluidic piston chamber area, which creates a negative pressure in that location and drives fluid in towards it. So pumping is achieved by drawing fluid in from whichever reservoir or location that is desirable, and that is achieved by essentially closing off all the valves except for the one that would lead to the location of the desired source of fluid.

In the preferred implementation the piston, of fixed dimension, is actuated by controllably switching from a given low pressure to a given vacuum. The low pressure and vacuum are from outside sources, and the displacement geometry of that piston structure determines the internal fluid volume displacement. Thus is provided a discrete, fixed-volume displacement per stroke. For a given stroke of the piston a fixed volume is displaced, either being drawn in or pushed out of the pump chamber. In a typical implementation, the volume is selected to lie within the range of approximately 300-600 nanoliters per stroke, per piston, controlled within a few percent of the selected value. A typical dimension is about 1 millimeter long by one half millimeter wide, of oval shape, with a deflection range of approximately +/−100 microns.

Operation of the device involves peristaltic-like pumping reagents and fluids from vented inlet reservoir sources. All sources and sinks are vented to atmosphere pressure. For example the buffer inlet reservoir, the detect inlet reservoir, and the sample inlet reservoir are all open reservoirs to atmospheric pressure. The waste is also vented to atmospheric pressure. Flow is created by combinations of valve and piston states always using valves and one piston to create a directional flow. For example, flow in direction to the waste is enabled by opening valves downstream of the piston towards the waste, blocking any upstream flow, and using the piston to push fluid in the direction of the waste chamber. Because of the venting described, there is no back pressure.

Flow can also be created back towards any of the inlets by closing valves downstream or on the waste side, opening valves on the inlet side and using the piston to push fluid back up.

For an example of a flow program, the valves and pump can be manipulated to move buffer liquid from the buffer inlet valve toward the waste and, alternatively, back into the detection reservoirs to use the buffer to rehydrate dried capture agent, e.g. detection antibodies, in the respective reservoirs. The system enables moving flow from any inlet to any other inlet or from any inlet to the outlet using combinations of valve and piston states, never having back pressure.

The piston operates on essentially a back pressure-less fluidic network because whatever direction the flow is desired to move in those valves are open to any of the inlets or outlets which are all vented to atmosphere.

An oval shape for the piston and its chamber provides compactness in the lateral dimension, the oval being arranged so that the long axis of the oval is in line with the straight channel, which corresponds to the long axis of the microcassette shown. Another benefit of the oval geometry is basically that it provides a region of the channel that progressively expands from the normal fluidic channel, expands out into this oval shape, and then it is re-constricted back to the normal channel dimensions, consistent with following laminar flow stream lines. For example, a typical channel dimension may be 150 to 250 microns wide up to the point where the piston chamber is located, and then expands in this oval shape over a length dimension of a millimeter, to approximately 500 microns wide, then narrows in similar fashion to the 200 micron channel width. The oval is made narrow, but still large enough to achieve the volumetric displacement needed for the assay, for example, 300 or 600 nanoliters. Keeping it thus narrow helps reduce pockets in which fluid can become trapped, or reach very low velocity, due to the velocity through the piston decreases because the total internal volume increases. When mixing is required or displacement of one reagent by another reagent is necessary, it is desired to keep fluid flowing through that channel, and to the extent that it is feasible to limit the width of that channel, the velocity through the pump can be maintained high enough to flush out the channel and not leave any behind while not requiring a large volume of fluid to complete the displacement of it. In the present implementation, it is desirable to employ widths between about 400 and 800 microns and the length between about 600 and 1200 microns, the smaller dimensions corresponding to the lower pump volume described.

The functions of the pumps and valves in this particular implementation are to perform an assay, an immunoassay involving filling a number of different aqueous reagent liquids through the channels which contain hollow flow elements with immobilized capture agent, e.g. antibodies. The purpose is to capture analyte, e.g. antigens of a particular type onto the surface.

Useful capture agents include antibodies, antigens, oligomers, DNA, natural DNA, or even small molecules for assays.

The following description is of a particular the immunoassay performed in a device according to the features described. The capture agent is selected in manner to have high affinity for a particular analyte that will flow within an aqueous sample, such as human plasma, human serum, urine or cerebral fluid. As the analyte of interest flows through the channel, actuated by a piston as described, a percentage of the analyte is bound to the inside surface of the hollow flow element, or a small number series of the elements, for instance between 3 and 10 elements, preferably 4 to 6. As that binding occurs, the concentration of that particular analyte in the fluid volume in and around the hollow element decreases, so it is desirable to replace that small slug of volume with fresh solution. For this purpose, the fluid is pumped through the system by cyclical actuation of the pistons and valves. By opening a valve close to the inlet and then applying a vacuum pressure to the piston, one is able to draw in a sample from a reservoir. As mentioned earlier, between 75 and 600 nanoliters is drawn in; in a presently preferred implementation, 200 nanoliters. In a present implementation, 200 nanoliters per piston stroke being selected, there are four pistons in the system, and since each one displaces 200 nanoliters, a full stroke of all four pistons provides 800 nanoliters per cycle.

There is one piston in each channel, and in the particular device being described, the device as depicted in the figures operates with four independent channels, so that would lead to four times 200 nanoliters per piston. The 800 nanoliters is drawn from whichever reservoir is being used at the time. If the sample is being flowed through the device, then every cycle will consume 800 nanoliters of sample, whether it is serum or plasma or another selected sample per cycle. The same is true if buffer or detection antibody is being flowed. It is always in these discrete volume displacements of 800 nanoliters per cycle, determined by the selected geometry of the piston design. The flow occurs in a pulsated-like manner because a piston will draw in 800 nanoliters, then it will push out 800 nanoliters, and then it will draw in 800 nanoliters, then it will push out 800 nanoliters, and so on, if unidirectional flow is desired. There are times during a typical ELISA protocol in which it is desirable to oscillate the 800 nanoliter fluid, in 200 nanoliter slug volume per channel, back and forth while within the channel without, in the net flow, actually displacing that slug with a new slug. That is performed simply by leaving all the valves but one closed, and then oscillating the piston back and forth. No net flow is allowed to go through the channels. The flow enters the channel, and then it is displaced back upstream, and then it is drawn back down and pushed back upstream in this cyclical manner. In a particular assay this is done approximately 60 times before the slug is discharged and a new slug introduced. This is done that 60 times in order to essentially utilize the analyte and its binding to the hollow flow element in an immunoassay.

Regarding the construction of the microfluidic device, FIG. 4A illustrates the multi subassembly construction wherein two unique subassemblies are created as independent standalone devices with rigid substrates supporting the devices. After their formation, they are brought together to create a completed assembly. Describing on the left side FIG. 4B, the pneumatic fluidic interface layer (a) consists of two components, a glass substrate in this case, and a polymer film bonded to the glass substrate forming the pneumatic channels and the fluidic interface channels to the outside world. That could also be constructed entirely as an injection molded plastic or embossed plastic member. The concept employs a solid rigid substrate with channels formed on one side. On to that is bonded a channel closure layer (b) which is also referred to as the membrane or the valve and piston actuation membrane. That is bonded in a permanent bonding mechanism using previously described processes—plasma bonding, PDMS to PDMS, or more complicated but similar in nature, bonding of mylar to PDMS. That would constitute a complete subassembly called the pneumatic fluidic layer. The second subassembly consisting also of a glass solid substrate and a PDMS sheet with channels cut into those where the PMDS sheet is bonded to the glass substrate to form what we call the fluidic reaction layer (c) in FIG. 4B. The idea here is that these two subassemblies are created, and they are standing alone in a mechanical sense. This affords the opportunity to place hollow flow elements into the open fluidic channels prior to bringing the fluidic subassembly into contact with the pneumatic subassembly. This has been done previously by bringing those two layers in contact with each other such that the PDMS channel layer on the fluidic device comes in contact with the PDMS membrane layer that has been bonded to the pneumatic device in a non-permanent bonding way, FIGS. 1A, 1B, 2A, 2B, 2C, 3A, 3B, 4A, 4B, 4C, 5, 6A, 6B, 7A, 7B, 7C, 8, and 8A. The bonding is of the nature of electrostatic adhesion between those surfaces to hold the two devices together. In that way the adhesion is counted on to be strong enough to prevent leakage out of the channels, but not so strong that overcoming that force at the valve is possible using a backing pressure. The valves thus are able to actuate by vacuum actuation off of the valve seat, the adhesion between the membrane and the valve seat being such that the vacuum overcomes the non-permanent electrostatic adhesion. This construction process thus involves the nonpermanent attachment of the two subassemblies relying on the self-adhesion between PDMS to PDMS brought in close contact to one another. The device operates well and allows the user to embed hollow flow elements or any other elements either round or spherical elements or any other type of device suitable to be placed into the fluidic channel prior to completing the channels by assembly the two subassemblies into contact with each other. The device works well. One of the advantages of the device is that the device is a reusable construction process so that after a particular assay has been run, it is possible to take apart the device, remove the elements that were used or consumed in the previous run and replace them with new elements—thus conserving the fluidic device, but replacing the consumable hollow elements. This gives the advantage of very rapidly running through assay performance tests using a minimum number of devices, giving cost effectiveness. It is useful for laboratories for investigations for instance in an investigating environment in which a laboratory is interested in dispensing or placing or spotting reagent or objects into the channels and then running an assay and repeating that process by reusing the microfluidic device.

The construction of the microfluidic device of FIGS. 1A, 1B, 2A, 2B, 2C, 3A, 3B, 4A, 4B, 4C, 5, 6A, 6B, 7A, 7B, 7C, 8, and 8A represent the concept of valves and pistons and the joining of subassemblies just described.

Figure 9A:
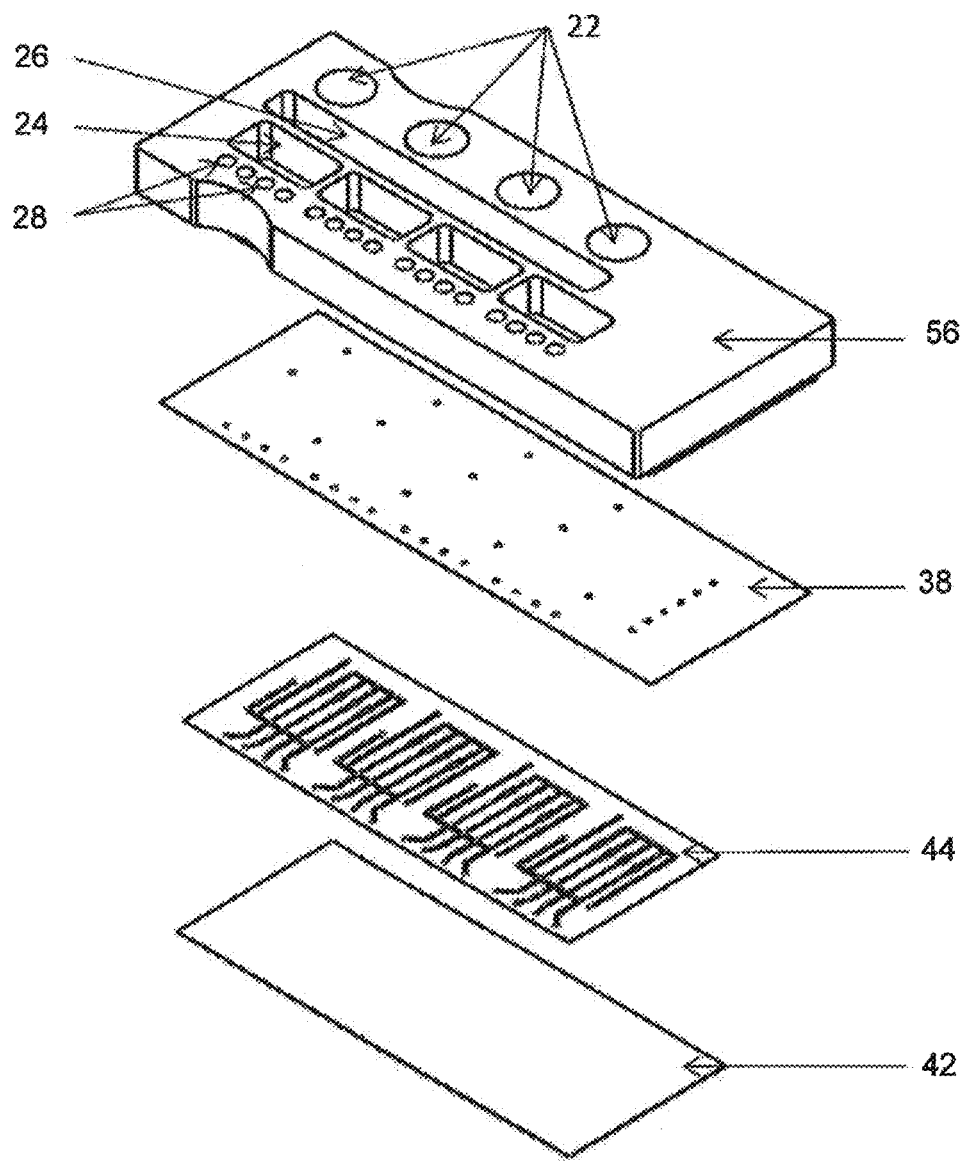
FIG. 9A—An exploded perspective view of the device of FIG. 9.

Referring to FIG. 9 et seq., another useful technique, with considerable advantage, of completing the assembly between two pre-constructed subassemblies, in contrast to using a non-permanent bonding process, is to form permanent bonds.

It is found that low pressure operation permitted by the general organization and design just described, can so-diminish the driving pressure on the air to permeate the membrane, that the bubble problem is lessened to the extent that an elastomeric membrane, such as PDMS, is employable with significantly reduced risk of air penetration and bubbles than designs of the prior art. This has the advantages of low cost and simplicity of manufacture, and enables achieving extremely consistent and sensitive assays.

A difference in the implementations now to be described is that the membrane or the flexible layer that is actuated by vacuum or pressure to operate the valves and the pistons is made from elastomeric material and different, advantageous techniques are used to fabricate the device.

Description of Special Hollow Flow Elements Produced by Batch Processes

One of the problems addressed concerns the surface area associated with a hollow flow element as has been depicted and as has been described above, i.e., an element having length less than 700 micron, preferably less than 500 micron, and in many cases about 200 micron, and a bore diameter between about 75+/−50 micron, that is fixed in a flow channel and exposed to flow of liquid sample. (Such hollow flow elements and assay devices based on them are available from CyVek, Inc., Wallingford, Conn., under the trade marks "Micro-Tube™, u-Tube™, and Mu-Tube™). Such devices are efficiently made of endlessly drawn microbore filament such as used to form capillary tubes, but in this case the filament is finely chopped in length to form discrete, extremely short hollow flow elements, rather than capillary tubes. It is realized that capture agent immobilized on the surface of such a device, applied by immersion techniques, can raise a significant depletion problem. This occurs, for instance, when attempting to characterize concentrations of an analyte at low levels such as a few pico-grams per milliliter, s is desired. The phenomenon referred to as "depletion" occurs in which the concentration of analyte in the sample being measured can be disadvantageously depleted volumetrically as a result of binding to a large active area of the flow element. This results in reduction of sensitivity of the assay, and therefore its usefulness. To explain further, any analyte in an ELISA or sandwich type of amino assay on antigen will bind to a capture antibody in a way that is governed by a kinetic reaction, a dynamic process. While analyte such as an antigen binds to capture agent such as an antibody, the reverse also occurs, the bound analyte molecules unbind from the capture agent. The kinetics concern an "on" rate and an "off" rate of analyte being captured and analyte being released. The capture reaction will continue, depleting the analyte in the ambient volume, and reducing its net rate of capture, until the system reaches equilibrium in which the rate of binding is equal to the rate of unbinding. The gradual action occurs according to a substantially exponential curve.

The absolute value of the equilibrium condition depends on the original concentration of the analyte in the volume of sample being assayed. Increase in concentration results in a higher signal, decrease in concentration results in a lower signal. In cases in which assay depletion occurs, the concentration of the analyte in the sample is detrimentally decreased over time. It is realized that hollow flow elements fixed in flow channel may present an excess of capture agent in the volume of liquid sample to which the element is exposed, decreasing the effective concentration of the analyte. The concentration decreases at an excessive rate, relative to initial, starting point concentration sought to be measured. While efforts to calibrate for this are helpful, such depletion ultimately lowers the sensitivity of the assay because, as the signal goes down, it approaches the noise level, and results in a lower signal-to-noise ratio, i.e. an inherent reduction of effectiveness of the assay. (Already there are significant contributors to noise i.e., background, nonspecific binding of capture antibody, fluorescence noise, electronic noise, etc.). Therefore, especially for detecting small concentrations, it is desired not to deplete the initial volume of the analyte in manner that does not contribute positively to the assay measurement. Efficient ways to do that, as by somehow limiting the amount of exposed surface have not been apparent. This may be seen as an inherent problem with use of small detection elements of various descriptions that are coated by immersion or the like and used in a immunoassay or sandwich assay or even a molecular diagnostic type of assay. One typically wishes to immerse the elements in capture agent, e.g. an antibody or some type of moiety that is a capture molecule for the analyte to be sensed or detected, to uniformly coat all surfaces of the element. One object of invention is to overcome this problem with respect to hollow flow elements characterized by an inside surface and an outside surface, or often also with two end surfaces. Adding up all surface area over which a density of capture molecules is coated can add up to a surface area on the order of over 100,000 square microns. This is the case for a preferred form of hollow flow element formed of small bore filament, the element having on the order of about: a length of less than 700 micron, preferably about 500 micron or less, and in presently preferred implementations, 200 microns. Likewise the inner bore is found desirable to have within a range of 50 micron+/−25 micron, for achieving uniform coating by iummersion and agitation. In one preferred case an element has an external diameter or width of 125 microns, and an internal diameter or width of 70 microns. A particular problem addressed here is to find practical approaches for accurately reducing active surface area of immersion-coated flow assay elements in general, and in particular, hollow flow elements, and in particular elements of the dimensions mentioned.

A further problem being addressed here concerns treated hollow flow elements that are to be in fixed positions in channels for exposure to flow of sample. It is desirable to expose the elements in batch, in free state to an immobilization process for applying the capture agent or antibody to the element surface, and then transfer each element mechanically to its fixed position in a channel, for instance in a channel of a multiplex micro-fluidic "chip" (or "cassette"). It is desired to use a quick and accurate placement process, for instance a pick and place device mounted on an accurate X, Y stage. For such purpose, it is desirable to physically contact the tiny element for picking it up from a surface and placing it in an open channel, which is then closed to form a micro-fluidic passage. It is desirable to employ grippers, e.g. a tweezer instrument, or a vacuum pickup that contacts the outer surface of the device. The pick and place action is made possible by pre-aligning open channels to receive the hollow flow elements and the surface on which the free elements are supplied with the automated pick-and-place instrument. This enables the grippers to pick up and place the hollow flow elements precisely from supply pockets to desired flow channel positions in which they are to be fixed. With a vacuum pick up, it is possible to serve the hollow elements in end to end abutting relationship in supply grooves, and engage the outer cylindrical surface with the vacuum pick up. We recognize a problem arises with having an active capture agent, e.g. antibody, immobilized on an outer surface of an element. Such a coating is susceptible to mechanical damage as a result of the manipulation process. Outside surfaces of micro-flow elements come in contact with (a) a supply surface, e.g. an aligning pocket or groove, (b) the transferring grippers or vacuum pickup device, and (c) surfaces of the channel in which it is being deposited. All of these contact opportunities give rise to possible damage to the fragile coated capture agent, which typically is a very thin layer of antibody or the like adsorbed to the surface of the flow element. This coating is often only a few molecules thick, thickness of the order of nanometers or tens of nanometers, and is quite fragile. The net result of damaging a capture surface of the placed hollow flow element is seen during read out of the assay. If the surface has been scratched or perturbed in any way, that can give rise to an irregular concentration or presentation of captured analyte, the signal can be irregular, and contribute to irreproducibility or poor performance of the assay.

We thus realize it is desirable not to have immobilized active capture agent on the outside surface of a hollow detection element, and especially the fine bore elements formed of micro-bore filaments, where it is susceptible to damage and where it contributes to increasing the total surface area of the capture agent or antibody that contributes to depletion.

The features described in the claims and hereafter address these and other important problems.

Discrete hollow flow elements are immersed in liquid containing capture agent, such as antibodies or antigens, and, after coating by the liquid, are picked and placed into channels for flow-through assays. The hollow flow elements are in preferred form of discrete elements of length less than about 700 micron, and bore diameter of 70+/−50 micron, preferably 50+/−25 micron. The flow elements are surface-treated so active capture agent, e.g. capture antibody, is not on the outside, or is of limited outside area. For this effect, the hollow flow elements are disposed in a bath of active agent and violently agitated, resulting in coating of protected inside surface, but due to extreme shear forces, a clean area on the outside surface, for instance the entire outside cylindrical surface of a round cross-section discrete element. In lieu of or in addition to this shear procedure, a special filament-manufacturing process is conceived that results in preventing coating an exterior surface of flow elements with a predetermined capture agent. Capture agent on selected coated areas are ablated or deactivated with precisely positioned laser beam, such as can be produced by a mask for simultaneous treatment of a large number of elements, leaving residual active agent of defined area on the inside surface of hollow flow elements. Residual capture agent, itself, on the inside of the elements, usefully defines a readable code related to the desired assay. Flow channel shape is sized relative to flow elements fixed in the channel to allow (a) bypass channel flow along the exposed outside of a hollow flow element to reach and flow through later elements in the channel in case of clogging of the first element, along with (b) sample and assay liquid flow through the hollow flow element to expose the surface to capture agent and other assay liquids. Lacking the need to attempt to seal the outside, the element can simply be gripped, as by an elastomeric sheet pressed against the element. Electrostatic attraction between flow element and channel wall is employed to fix the element in position, overcoming any disturbing force of the placing instrument as it is drawn away after delivery of the element. After assay, in the case of use of epi-fluorescent detection, fluorescence is excited and read by special scanning confined to the hollow flow element geometry. Locators are seeded in the recorded data, and used to locate the regions of interest in detected fluorescence data, e.g. from the elements. Code, written with the capture agent substance inside the hollow element is read through a transparent wall of the element. A number of the features are or will be found to be useful with other hollow elements, for example, longer elements.

In respect of scanning, the purpose of this invention to deliver a method for performing a fluorescence measurement of multiple immobilized elements contained in a microfluidic chip. This method provides for determining the paths to be followed during the scanning, as well as the proper focus, and camera exposure. The method is based on a known general chip layout. The method provided results in the ability to place the chip to be measured into the scanner and then start the scan without any additional manual settings required. The method does the rest, and produces the desired fluorescence measurements as the results.

Certain aspects of invention involve eliminating or preventing the occurrence of active capture agent on outside surfaces of the hollow flow elements, e.g. extended outside cylindrical surface, and/or end surfaces, while leaving active capture agent on the inside surface unperturbed, or of a desirable area or pattern. Features addressing this aspect include techniques to selectively limit the capture agent on the interior surface and steps that act in combination with outside and inside surfaces to achieve the desired result.

For the specific advantage of reducing the overall capture surface area, two aspects of invention will be described, and the effect of their combination. A first technique is employed to eliminate or prevent capture agent, e.g. antibody, from immobilizing to the outside surface of hollow flow elements. That is done during a batch coating process, and involves suspending discrete hollow elements in an Eppendorff tube or other laboratory tube with the capture agent of interest and aggressively agitating fluid to impart disrupting shear forces to the exterior surface of the elements. Preferably this is achieved by vortexing the fluid at high speed, for instance employing an instrument that orbits the container at approximately 2000 rpm of the orbiter, about an orbital path with total lateral excursion of the supporting table of the order about 0.5 cm, measured across the center of rotation of the orbiter.

The hollow flow elements are placed with a volume, e.g. a milliliter of capture agent, e.g. antibody. The appropriate vortexing speed is dependent e.g. on the nature of the suspension, e.g. the viscosity of the liquid chosen, and can be easily determined experimentally. It is set by observing whether the capture agent is effectively non-existent on the outside, long surface of the hollow flow elements, e.g. the outside cylindrical surface in the case of the body being of circular cross-section.

The physical principle involved concerns shearing force on the outside surface of the element that acts to prevent binding of the capture agent to the surface through an adsorption process. One can observe whether the vigorous agitation is sufficient to shear off any capture agent, e.g. antibody, that has already been bound to that surface. At the same time, the inside surface is environmentally shielded from this shearing by virtue of the geometry which is tubular, and the micro-bore of the tube. This prevents vortexing from causing any turbulence to occur within the element. Only laminate flow conditions exist. With micro bore elements the Reynolds number is always low enough to ensure that laminar flow condition exists on the inside surface. Under these conditions, the velocity of fluid traversing in the hollow element at the interior wall interface is by definition zero. So there is no shear force involved there, whereas the outside is in a highly turbulent, high shear force environment. The shortness of the length of the elements enables substantially uniform coating of the inner surface, whereas longer elements, coated by immersion, are susceptible to detrimental non-uniform coating.

The observed result of aggressive agitation, e.g. vortexing, is that fluorescence which is observed by performing a sandwich assay is completely absent from the outer cylindrical surface, or other shape of a hollow element, whereas it is present in an observable way on the inside surface. In the case of square-end hollow flow elements, fluorescence is also present on the end faces of elements.

Vortexing is the presently preferred technique for producing the shear forces. The case shown here employs orbitally rotating the coated element in a very rapid manner back and forth in small circles at a rate of approximately a couple thousand rotations per minute, and an excursion of about 25 mm.

However, any type of rapid oscillation that creates a high degree of turbulence can be employed, so a back and forth motion, a circular rotation, anything that would very rapidly mix the fluids and create high shear forces will suffice.

In summary, hollow flow elements in the presence of aggressive agitation leads to removal of capture agent, e.g. antibodies, from outside surface of the elements, and prevention of their coating with the agent, but leaves the inside surface of the element in condition to immobilize capture agent, e.g. capture antibodies, for subsequent interaction with analyte of the sample.

As an alternative to the high shear technique, we conceive an alternate process in which, during the original drawing of the small bore tube, and prior to the point along the draw path that the usual removable protective polymer coating is applied to the filament, that a non-stick coating, e.g. sputtered gold, silver or graphite, is applied to the filament, e.g. by passing through a sputtering chamber. Silane or similar coating must be applied to receiving surfaces before capture agent, e.g. antibodies will attach. However, due to the properties of the sputter coating, or the like, the surface will not receive the silane or equivalent, then likewise, the active capture agent.

Another feature of invention concerns realizing the desirability and technique of removing coated capture agent from selected end surfaces of the flow elements and a margin portion or other portion of the interior surface. Preferably, following the aggressive agitation process, the elements are further processed using a laser elimination process that removes or de-activates capture agent, e.g. antibodies, from surface from which the agent was not removed by the high shear process. Those surfaces include transverse end surfaces and a selected portion of the inside surface, leaving only an annular stripe on the inside surface sized sufficient to process the assay, but small enough to reduce depletion of the analyte from the sample.

In a preferred form an ablating laser is arranged transversely to the axis of elongation of the hollow elements with the effect that the energy arrives though parallel to the end faces has a neutralizing or removal effect on the capture agent that is on those end faces, as a result of incidence of substantially parallel radiation, but also of internal reflection scattering of the radiation by the transparent substance that defines those end faces.

The net effect of two novel processes described, if used in novel combination, is to leave only a band of selected dimension, which can be small, of capture agent immobilized on the inside surface of the hollow element. This can be done in a way that leaves one or more bands separated by a space of no capture agent. Thus one can generate a single band in the center or a single band closer to one end or multiple bands distributed along the length of the element. These bands can be of different widths and can have different spacings and can be of the form of a code, e.g. a bar code, which is useful to encode the particular flow element.

Further is a description of manufacturing techniques that have important novel features.

The short, hollow elements are first formed i.e. chopped, from previously-supplied continuous small-bore filament into the short, discrete elements. They are then treated in batch manner.

A bulk of the hollow elements is then exposed in an Eppendorff tube to wash buffer. After washing processing is performed, the buffer is removed, and replaced with a silane. By use of this simple, low-cost immersion step, the silane is allowed to bind to all of the surfaces of the elements. Excess silane after a period of time is washed away with water in a buffer. Then a capture agent, e.g. antibody, in solution is added to the Eppendorff tube with the bulk of hollow elements and allowed to incubate over night. The incubation is performed on the orbital vortexer for approximately 16 hours at 2000 rotations per minute, the order of 0.5 centimeter diametric dispacement by the orbital motion. The orbital plate that contains the numerous Eppendorff tubes is approximately 6 inches in diameter, but the orbital motion is a circular pattern counterclockwise and then clockwise motion the orbiting causing the displacement of approximately 0.5 centimeters from side to side, for instance.

After the vortexing process is completed, the net result is that the capture agent has been immobilized on the inside surface of the hollow element and also on the end faces but it is not present on the outside cylindrical surface of the hollow element. The capture agent solution is removed from the Eppendorff tube which is replaced with a wash buffer, a wash buffer solution, and the wash buffer solution is then further replaced with a stabilizing buffer, what we call a blocking buffer. In the preferred embodiment a commercial material called STABLE COAT solution is used.

STABLE COAT blocking solution is introduced to the Eppendorff tube along with hollow flow elements, then a portion of those elements is aspirated in a pipette along with some of the STABLE COAT, and dispensed onto an alignment plate. For tweezer pickup the alignment plate contains a series of rectangular shaped pockets, each designed to accommodate and position a single element within a small space, preferably with clearance tolerance sized in microns, a space of 10 to 50 microns between the element and the walls of the pocket. After the elements are allowed to roam on the plate, they fall into these pockets still in the presence of the buffer solution. The excess buffer solution is removed from the alignment plate containing the elements by placing their plates with elements into a centrifuge or centrifuge holder and centrifuging at approximately two thousand rpm, for 30 seconds, thereby removing all excess STABLE COAT solution from the plate and the elements. This process is facilitated by the novel design of the plate, in which drain channels extend radially from the pockets.

(In the case of vacuum pickup continuous grooves are employed to receive the treated elements, in greater density than enabled by the pockets, as the elements can be close together, end to end, since pickup will be by engaging the cylindrical surface, not the end surfaces as is the case with tweezers.)

The hollow elements while still in the plate are further processed with a laser, preferably an ultraviolet laser, which could be an excimer laser, fluoride or krypton fluoride laser, with two beams that are spaced such that the ends and an end margin portion or section of the element are exposed perpendicular to the element axis by a laser beam in a way that either ablates or denatures the capture agent, e.g. antibody, from the ends of the element as well as a section of the inside surface of the element. It is a feature of the laser configuration that the two laser beams are separated by a fixed distance that define the desirable width of the remaining band of capture antibody surface. The hollow elements within their pockets of the alignment plate can be allowed to move back and forth with a degree of liberty, while still the laser processes substantially the ends of the elements and leaves a fixed width pattern near the center of the element, plus or minus a reasonable tolerance window.

It is possible instead to define a series of three or more laser beams, with gaps, such that the pattern produced by the various widths of laser beams in the various gaps between the laser beams defines a pattern of exposure in the hollow element that looks like and is useful as a bar code.

Further, it is realized as useful to have significant by-pass flow in a channel outside of the hollow element as well as through the element. One advantage is simplicity of manufacture as the element can be held but without being sealed and with no attempt to use cumbersome adhesive to adhere the element to the channel walls. Another advantage is the avoidance of the risk of totally spoiling an assay because a chance particle obstructs internal flow of one of the hollow-flow elements when arranged in series in a liquid flow path. Having significant by-pass flow on the outside, at least as great as 50%, in many cases 75% or larger, and in certain preferred instances 100% or more is highly useful. As least to some extent this enables "short circuiting" the element, ensuring that despite one element being plugged or obstructed and flow stopped, the other elements will receive flow and the assay will only be partially affected by the obstructing particle. It is realized further that with concepts presented here, enabling the avoidance of having active capture agent on the exterior, i.e for cylindrical elements, on either the cylindrical exterior of the hollow element or on its end faces, does not result in a depletion problem. The techniques previously described, of avoiding active capture agent from adhering to the exterior cylindrical surface of the hollow elements and laser treating the ends, thus contribute to the practicality of employing the by-pass flow described.

Sizing of Hollow Flow Elements

It has long been accepted knowledge that the smaller the surface area of the capture agent, e.g. antibody, the more sensitive the assay is from a theoretical point of view. The desire has always therefore been to keep the inside diameter of a hollow element as small as possible to minimize that surface area. But it has now been determined empirically that, within limits, the performance of the assay is improved as that diameter is increased to an extent. It is believed this is a direct result of non-uniform coating by the batch process desired to be employed, as well as probably some effects that occur during the assay in that it is possible that there are perturbations in the amount of volume, total volume, that actually flows through the hollow elements in cases where the tube element diameter is small compared to an element of i.d. of 75 microns. We have found that the internal diameter should be about 75+/−50, and in preferred cases, 50+/−25.

It is preferable that the exterior diameter have a diameter or width within the range of 1.2 and 4 times the internal diameter or width.

For length of the hollow flow elements, best results are obtained with lengths of less than about 700 micron, and in many cases, less than 500 micron. In a presently preferred form the length is 250 um.

100. I will check that while we are talking. In the earlier application, the ratio of 20 to 1 was set to be ID length to ID of 20 to 1 was said to be preferred.

It has been discovered that the shorter hollow elements lead to greater uniformity of the coating of capture agent when coated by the batch process described herein, and as well, shorter hollow elements are found to be more amenable to withstanding axial tweezing forces during pick and place motions.

As previously mentioned there are significant advantages in providing two subassemblies that are each fabricated on their respective solid substrates or carriers, which are dimensionally stable, though permissibly flexible. The extremely small hollow flow elements (or other detection elements to be fixed in position within the cassette) are placed into open locations on the mating face of one of the subassemblies, prior to aligning. Once the subassemblies are aligned, the two subassemblies are brought together under bonding conditions to form one completed assembly, and fixing the embedded location of the elements. Then the two subassemblies are brought together to complete the fluidic channels. Bringing them together completes the valve and piston devices as well as embedding the detection elements. These features occur with the non-permanently bonded implementation, previously described with reference to FIGS. 1A, 1B, 2A, 2B, 2C, 3A, 3B, 4A, 4B, 4C, 5, 6A, 6B, 7A, 7B, 7C, 8, and 8A.

Another implementation of the broad assembling concept will now be described, employing permanent bonding features. We will refer now to the Figures beginning with FIG. 9. The following is a list of components called out in FIG. 9 et seq.

20. Completed Cartridge
22. Sample Inlet wells
24. Buffer Inlet Wells
26. Waste Well Reservoir
28. Reservoir Well—Detect Antibody Reagent—Preferred Embodiment—Dried
30. Microfluidic Channels
32. Extremely Small Hollow Flow Elements ("Elements")
34. Microfluidic Valve Seats
35. Microfluidic Valve Pneumatic Chamber
36. Piston Fluidic Chamber
37. Piston Pneumatic Chamber
38. Elastomer Membrane
39. Plasma Bonded Interface
40. Arrows Depicting Flow
41. Bypass Flow Path
42. Glass Substrate
43. Bulk Material
44. Microfluidic Channel Walls
46. Control Reservoir Layer
48. Fluidic Layer Sub Assembly—No Elements
50. Fluidic Layer Sub Assembly—With Elements
52. Single Sample Four Analyte Microfluidic Network
54. Microfluidic Valve—Full Assembly
55. Piston—Full Assembly
56. Reservoir/Control Plastic Member
58. Pneumatic Interface Ports
60. Piston Control Lines
62. Valve Control Lines
64. End of arm tooling (tweezer or vacuum probe)
66. Pick and Place Arm (moves up and down)
68. Source/Target X,Y table (moves in X and Y coordinates)
70. Source of Hollow Flow Elements (groove or well plate)
72. Target Microfluidic device
74. End of arm tooling—vacuum
76. End of arm tooling—tweezer
78. Activated Surface In FIG. 9, starting from the upper side, the subassembly 46, i.e. the controls/reservoir layer 46, is comprised of two elements, the upper injection molded or machined plastic component 56 with a PDMS membrane sheet 38 bonded to its lower surface.

The bottom fluidic layer or subassembly 50 has detection elements, e.g. hollow short cylindrical flow elements 32. The fluidic subassembly consists of a thin glass sheet 42 with a PDMS gasket or sheet permanently bonded face-wise to its upper surface, the sheet having cut-outs defining fluidic channels between channel walls 44, the channel bottomed on the glass sheet 42, FIG. 10C. Before those two subassemblies are brought together, the detection elements are dispensed, in the embodiment shown, by pick and place action, into fixed positions in the channels of the fluidic layer 48. The two subassemblies 46 and 50 are brought together and bonded in a way that provides fluid-tight and leak-free operation, but also enables the actuation of valves and pistons by portions of membrane 38. One novel feature of this construction is that the two subassemblies as described, using a PDMS gasket, enables capture or embedding detection elements, here extremely short hollow flow elements, (Micro-Tube™ elements) into channels. Combining those two subassemblies into a single assembly provides the functionality of having microfluidic channels that contain the hollow flow elements as well as functioning valves and pistons. In a fluidically robust and leak-free microfluidic structure, using the plasma-bonding process, known per se, to perform the numerous functions described, securing the detection elements in place and forming the valves and pump diaphragms in a way that completely seals the channels, together with a process to be described that defeats plasma bonding at the exposed valve seat contacted by the PDMS membrane.

The fluidic subassembly is assembled by covalently bonding PDMS to glass, then upper assembly, the reservoir assembly is formed by covalently bonding PDMS to plastic. The dominant advantage is the placing the discrete, small detection elements, the hollow flow elements, into open channels prior to assembling.

The importance of the technique also relates to enabling the immobilization of capture agent, e.g. antibody, onto a solid substrate in an efficient batch process, thereby allowing many thousands of these elements to be fabricated in one very simple batch process which is cost effective and highly reproducible. The process itself is absent of process parameters that would cause damage to biological content, and can be a room temperature process.

Thus features of the concept include bringing together subassemblies to capture elements in a fixed position, the capture (or detection) elements having been pre-prepared in batch process, with the final assembly, which employing a bonding process, especially the permanent plasma bonding process to join the subassemblies, and doing it in a selective way at the valve seats by repeatedly locally deflecting and bringing in contact the valving surfaces, which will now be described.

Valve Break-in Process

Connect pneumatic control input ports to externally controlled pneumatic line/s

Actuate all valves using vacuum (5-14 psi) so as to draw membrane up into pneumatic valve chambers.

Bring surface-activated (e.g. plasma activated) Reservoir/Control layer into conformal contact with Fluidic Layer.

Momentarily apply pressure (1-10 psi) to valve control lines so as to force PDMS membrane into intimate contact with the PDMS surface of the Fluidic layer. Allow contact for approximately 1-3 seconds before switching back to vacuum pressure in control lines.

Perform initial break-in of valves by rapid performing a sequence of actuations between vacuum and pressure for approximately 20 cycles, over a time period of 1-2 minutes.

Continue to cycle valves with vacuum and pressure over a period of 5-20 minutes, depending on the surface activation and thermal history of the PDMS surfaces. Once the initial break-in cycles are performed, a slower and more protracted actuation sequence is preferably used to prevent the slow inexorable bonding of the PDMS surfaces, until all inclination for bonding is prevented, which can be achieved by actuating the valve with pressure for up to 1 minute followed by intermittent actuations with vacuum so as to break any newly formed bonds. Continuing this process for up to 20 minutes has been shown to completely prevent future permanent bonding between the valve membrane and the valve seat.

Other materials which have molecular bonding capabilities when like surfaces are bought together may also be employed, and the molecular bonds destroyed at vave seats in similar manner, Description of Valve Break-in Process Native PDMS, comprised mainly of repeating groups of —O—Si(CH$_3$)$_2$—is hydrophobic in nature, and, without special treatment, has a tendency to adhere to, but not permanently bond to other like surfaces such as PDMS, glass and silicon. However, upon treatment with oxygen plasma or the like the methyl groups (CH$_3$) are replaced with silanol groups (SiOH), thus forming a high surface energy, hydrophilic surface capable of bonding irreversibly with other like surfaces containing high densities of silanol groups. This irreversible bonding process occurs via condensation reaction between OH groups on each surface resulting in covalent Si—O—Si bonds with the concomitant liberation of water (H$_2$O).

Oxygen plasma and similar techniques have control parameters such as pressure, power and time all of which determine the concentration of surface OH groups. Higher concentrations of OH groups lead to more covalent bonds between the two surfaces and therefore higher mechanical bonds. Left exposed to atmosphere after oxygen plasma or similar treatment, the hydrophilic surface will undergo "recovery" back to its native hydrophobic state via migration of short, mobile polymer chains from the bulk to the surface. Full "recovery" occurs over a period of hours at room temperature and can be accelerated with increased temperature and retarded by storage in vacuum and/or low temperatures. This is accommodated by storing activated substrates at −50C in vacuum bags for several days to lock-in the hydrophilic surface treatment prior to bonding.

Since the bonding mechanism follows a fairly slow condensation reaction which involves the liberation of water over a period of several minutes to a few hours before completely consuming the available OH sites, it is possible to interrupt this process before completion. Once completed, the bond strength between the interfaces is comparable to the bulk tear strength leading to an irreversible attachment of the two materials. Attempts to separate the layers at this stage will lead to bulk damage of one or both of the layers. However, interruption of the bonding process by mechanically separating the surfaces during the early stages of the bonding cycle is found to irreparably damage only the small number of formed bonds between the two surfaces. The tear strength of the bulk is considerably higher than the interface bond, therefore separation produces no irreparable damage to the bulk. Also, if the bonding process is interrupted early enough (typically in first few seconds), then the force required to separate the layers is little more than the adhesion force required to separate untreated layers. Bringing the layers back into contact for a short duration (typically a few more seconds), will initiate and interrupt bonding again. Each time this cycle is repeated, potential bonds are incrementally eliminated until all such bond sites are consumed and the material reverts back to having the properties of the untreated material.

In a preferred novel technique, microvalves are formed between layers of PDMS by surface activating, e.g. plasma activating, the PDMS or similar surfaces, bringing them into contact and then activating the valves to open and close in such a manner that permanently disrupts bonding between the flexible membrane and the valve seat, but results in complete and robust bonding elsewhere over broad surfaces to hold the device together.

Device Manufacture

Referring to FIG. 9, a product employing the concepts described is a consumable microfluidic cartridge for the purpose of quantifying antibody concentrations in human plasma samples. The cartridge, such as shown in FIG. 9, contains on board provisions for sample inlets, in other words, a reservoir that will receive a sample to be analyzed, e.g. a blood plasma or serum sample.

A completed cartridge 20 contains sample inlet wells 22 for receiving a patient plasma or serum sample or other type of bodily fluid, including cerebral spinal fluid, or urine. It will also contain a buffer inlet well 24, buffer being a reagent used during the processing of the assay, a waste reservoir well 26 designed to contain all of the reagents and sample that flow through the microfluidic channels and that are no longer needed all self-contained on the microfluidic cartridge, also containing a reservoir well 28 which has contained in it a detection antibody with a fluorescent label. The preferred embodiment, the detection antibody will be dried down in the channel or in the reservoir and rehydrated during operation using the buffered contained in buffer well 24.

Figures 10A, 10B:
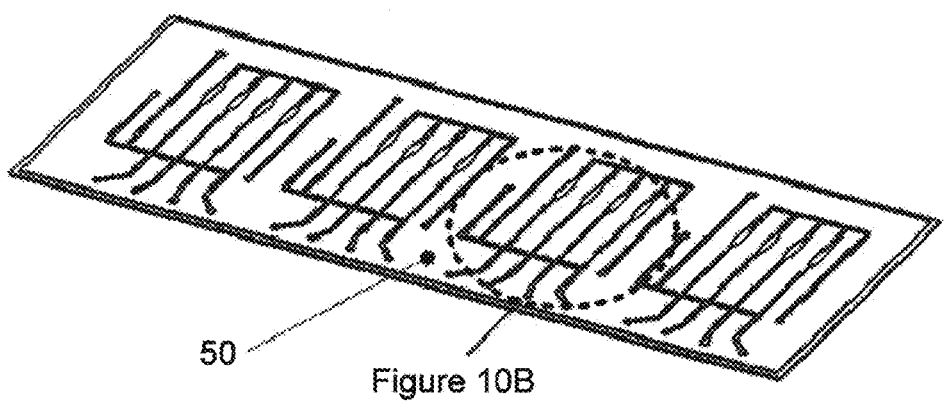
Figure 10B:
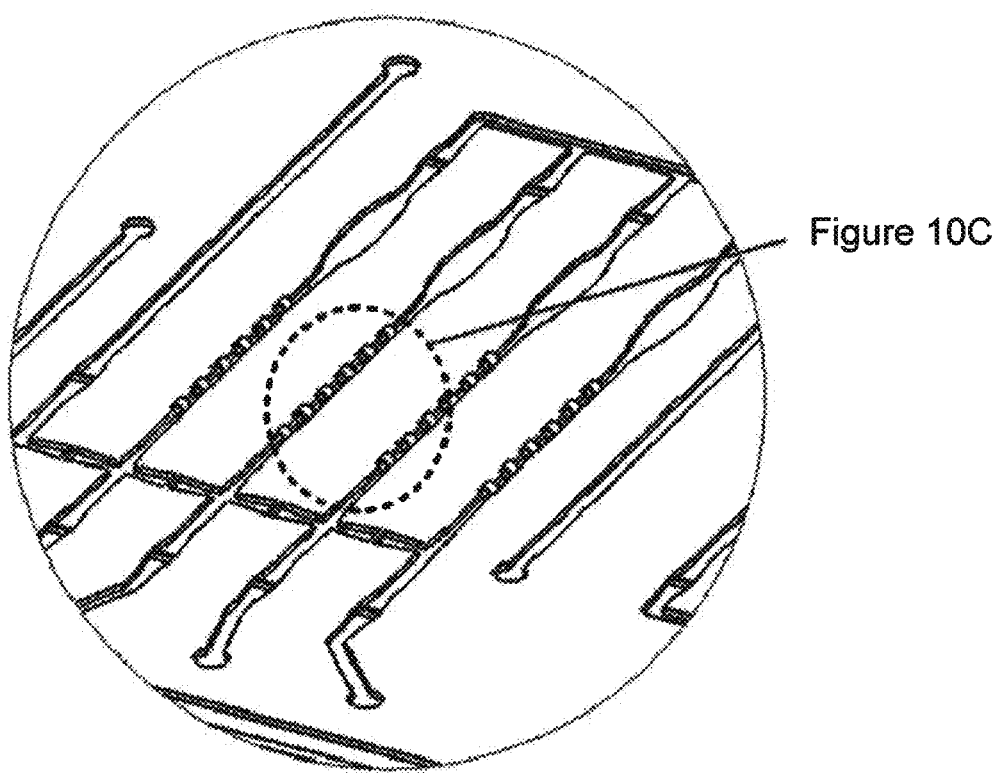
Figure 10C:
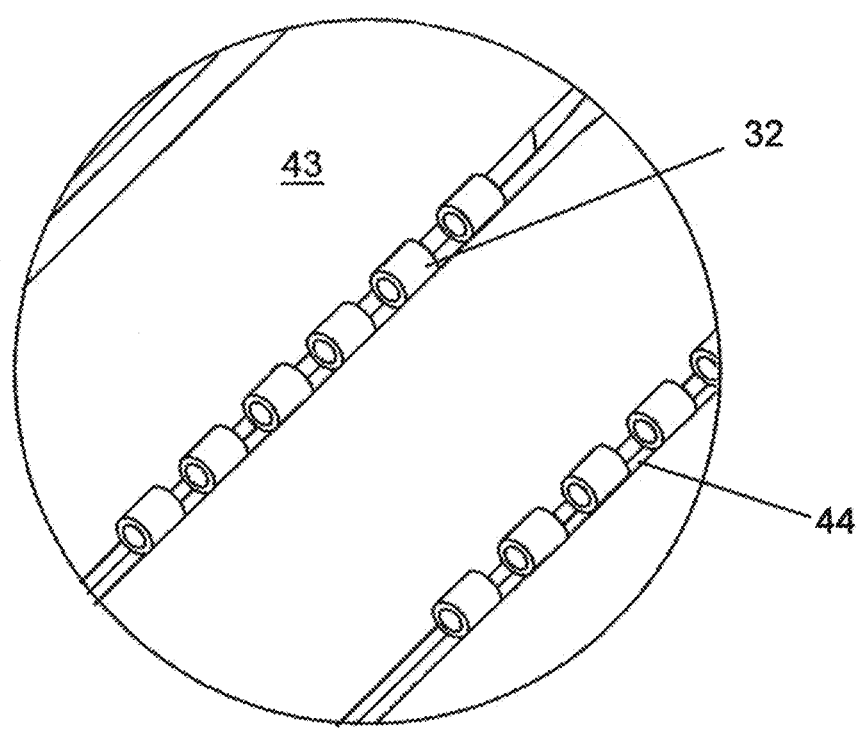
FIG. 10C—An even more greatly magnified view of as single extremely small hollow flow elements disposed in a channel of FIGS. 10A and B.
Figure 12:
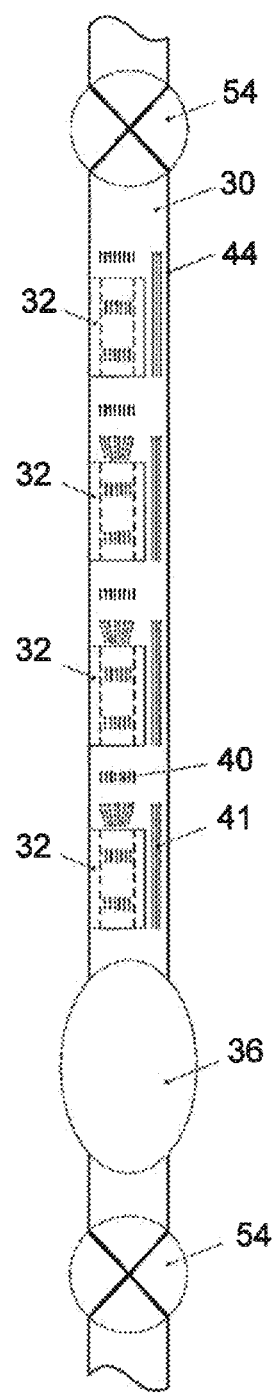
FIGS. 12 and 12A—Plan views of a single channel, with schematic illustration of on-board pump and valves, and showing flow paths through and alongside hollow flow elements.
Figure 12A:
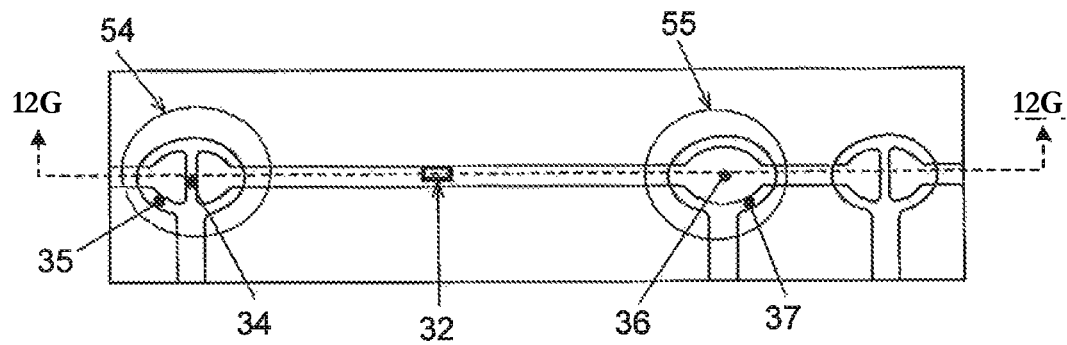
Figure 12G:
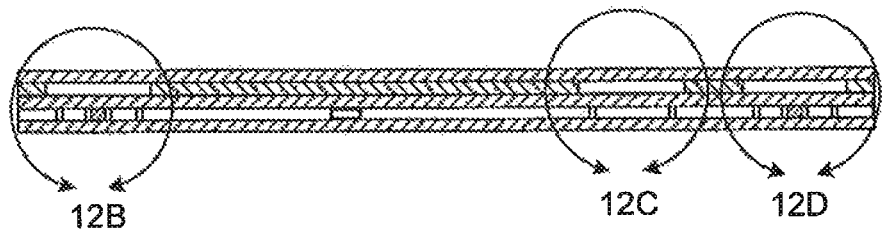
FIG. 12G is a cross section view of FIG. 12A denoting the regions in which the magnified views of the FIGS. 12B, 12C and 12D are taken.
Figure 12B:
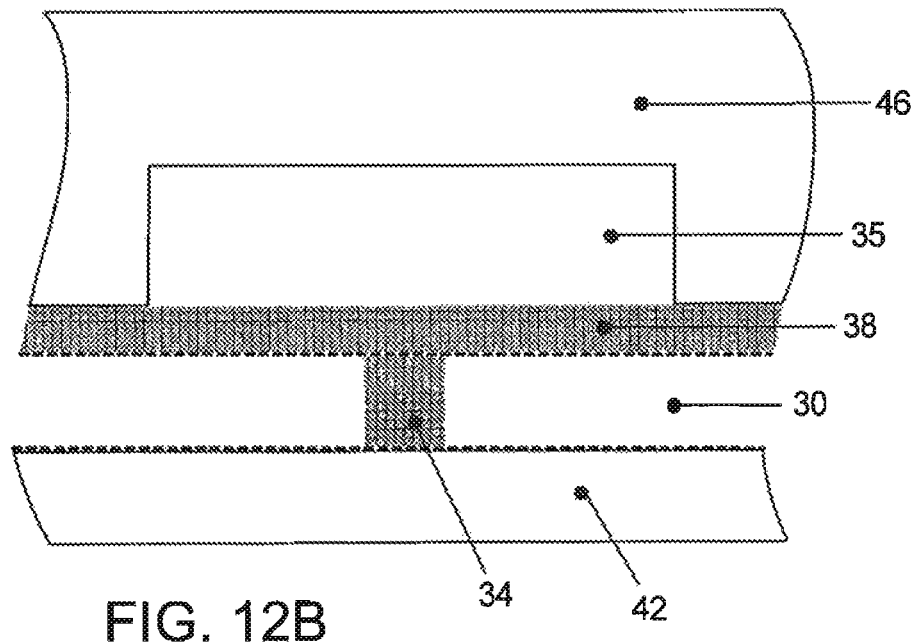
FIGS. 12E and 12F—views similar to FIGS. 12B and 12C, respectively, in another state of operation.
Figure 12C:
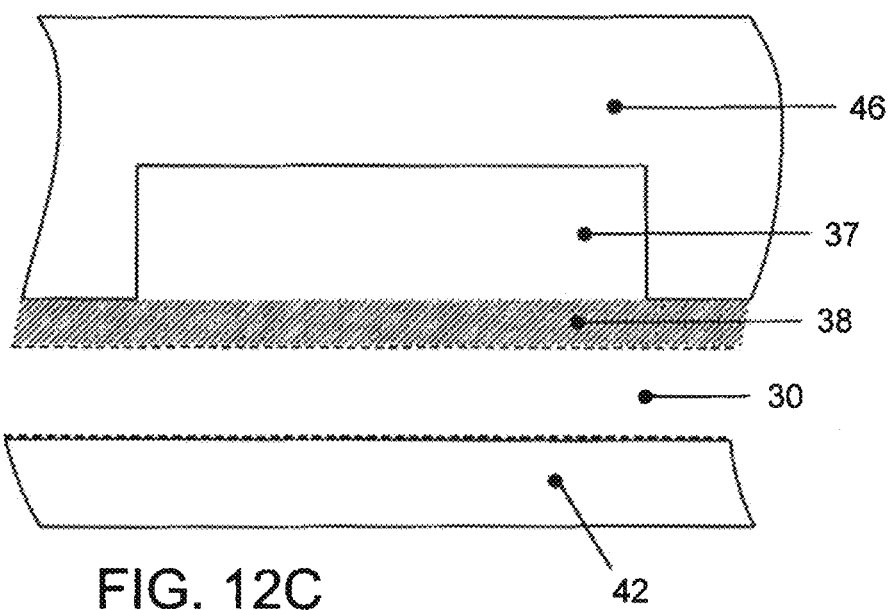
Figure 12D:
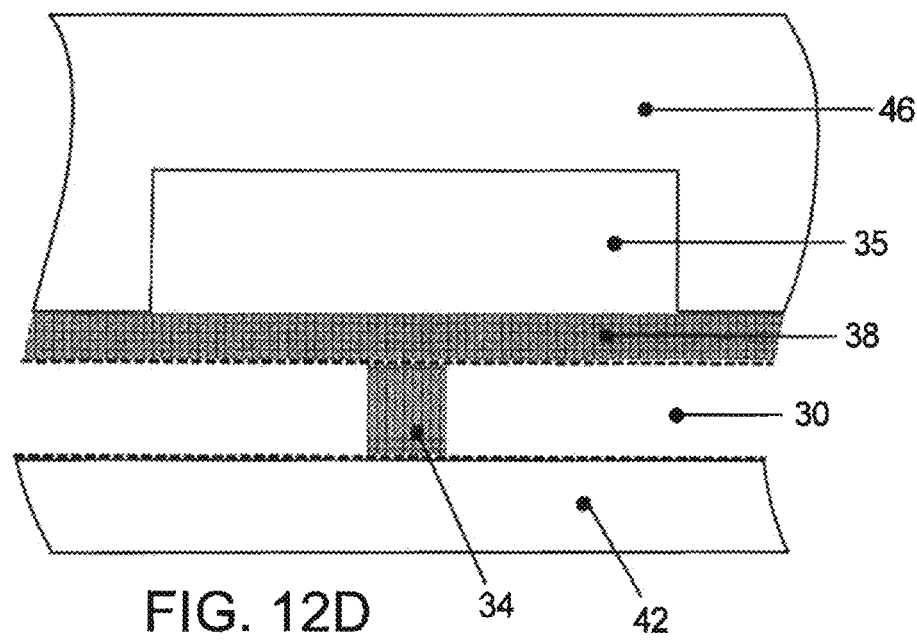
Figure 12E:
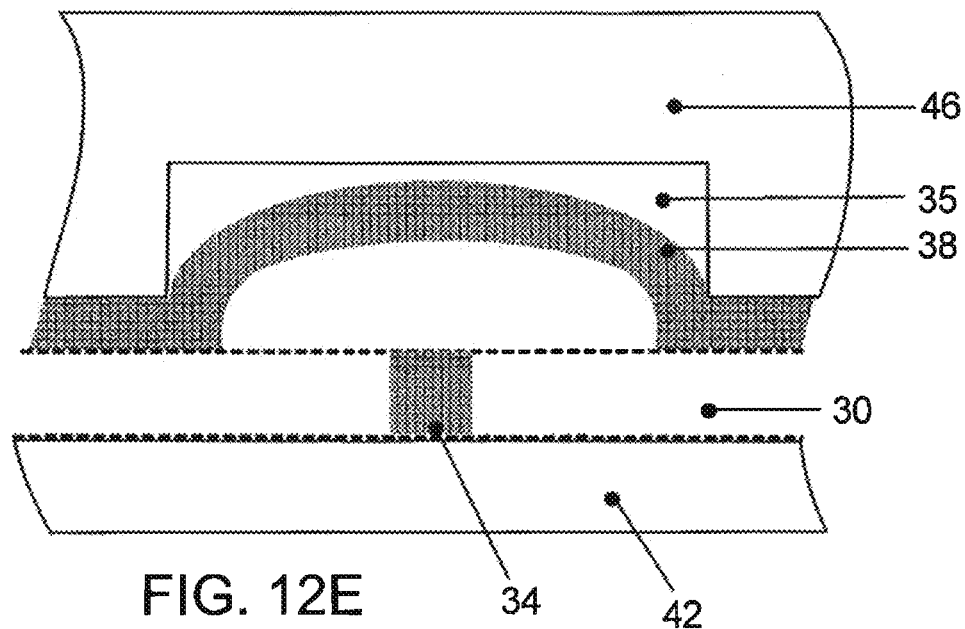
Figure 12F:
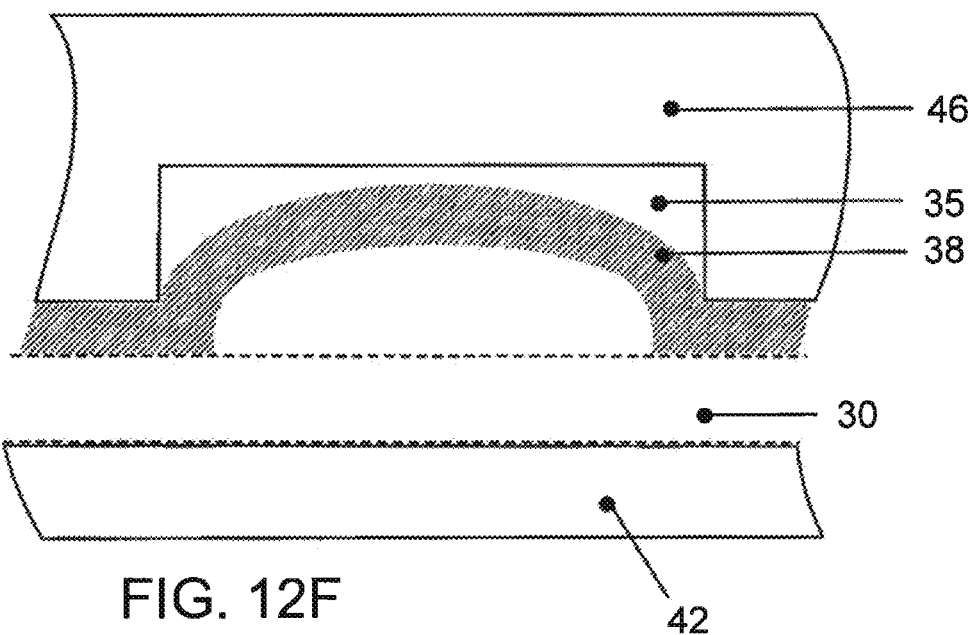

Referring now to FIGS. 10, 11 and 12. FIG. 10 shows the microfluidic channels containing 4 independent microfluidic channel groups containing the extremely small hollow fluidic flow elements, referred to hereafter as elements. FIG. 10 shows those four channel groups each containing six channels 30. There are extremely small hollow flow elements 32, microfluidic valve seats 34 and pistons 36. The extremely small hollow flow elements are formed in a batch process with a capture antibody provided on the inside surface of the elements, and those elements are placed into channels 30.

Example of dimensions of the hollow elements: The length of the preferred embodiment is approximately 250 microns, the inner diameter approximately 75 microns, and an outer diameter of approximately 125 microns. FIG. 11 is a blown up schematic of the hollow elements shown in two parallel example channels.

In presently preferred practice the channels are wider than the elements, and the elements are attracted by near electrostatic force to adhere to one channel wall, defining by-pass flow paths on the other side.

Figure 13:
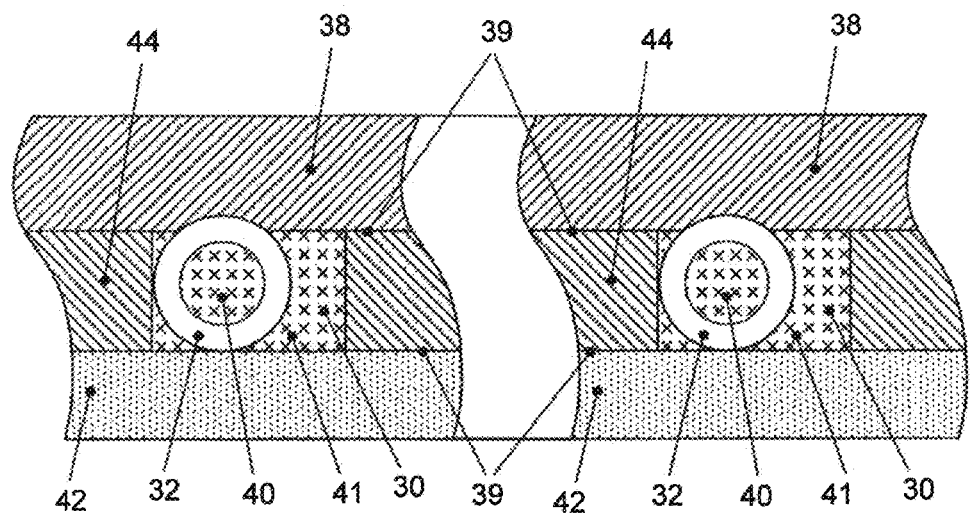
FIG. 13—A diagrammatic cross section, with parts broken away of channels of a device, and depicting lines of flow through and outside the flow element.
Figure 13A:
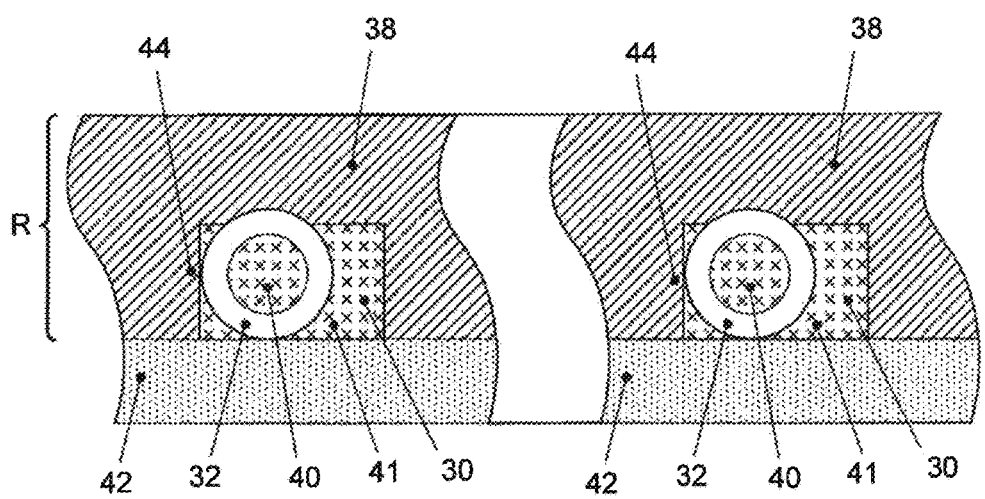
FIG. 13A—A view similar to FIG. 13 in which two layers (38 and 44) have been fused by covalent bonding to close the channels and secure the hollow flow elements.

FIG. 13 shows a cross-sectional view of a hollow flow element in channel 30 with space surrounding hollow element on the outside of the element. FIG. 13 depicts hollow element 32 in microfluidic channel 30 with flow arrows 40 depicted, the hollow element as captured by the top surface elastomer membrane 38 and on the bottom surface by glass substrate element 42.

Typical dimensions for the glass substrate layer 42 are 200 microns thick of boro-silicate glass and the elastomer membrane layer element 38 has typical thickness of 100-200 microns. Also providing the channels are an elastomer PDMS material typical 100-150 microns tall thus forming the microfluidic channel. Also shown in FIG. 13 the elastomer membrane layer continues both to the left and to the right as well as the glass substrate continuing to the left and to the right and on either side containing one or more parallel microfluidic channels also containing hollow glass elements, glass layer element 42 is bonded to elastomer wall, a micro-fluidic channel wall 44, previously formed in a sub-assembly process using a covalent bonding technique involving plasma activation of the PDMS surface and subsequent contacting and therefore bonding to the glass layer, the hollow element is inserted into that channel.

There are additional channels 30 in parallel. The purpose of parallel channels is to isolate different antibodies from each other for preventing cross-reactivity.

Channel depth is less the diameter of hollow element that are picked and placed against one of channel walls such that electrostatic forces between the element and channel walls release the placing device, e.g. tweezers or vacuum pickup, from the element. In this process, by moving in an "L" shaped motion, laterally at the end, increases the electrostatic attraction and allows the tweezer to be released from engagement with the element and tweezers to be removed. Channel 30 enclosed by bringing into contact both ends of elastic membrane 38 of control/reservoir 46. Elements are retained in channel 30 between elastomeric 38 and glass 42.

FIG. 11 shows schematically two example channels containing a series of four spaced apart elements 32 and by-pass flow space 41.

Figure 14:
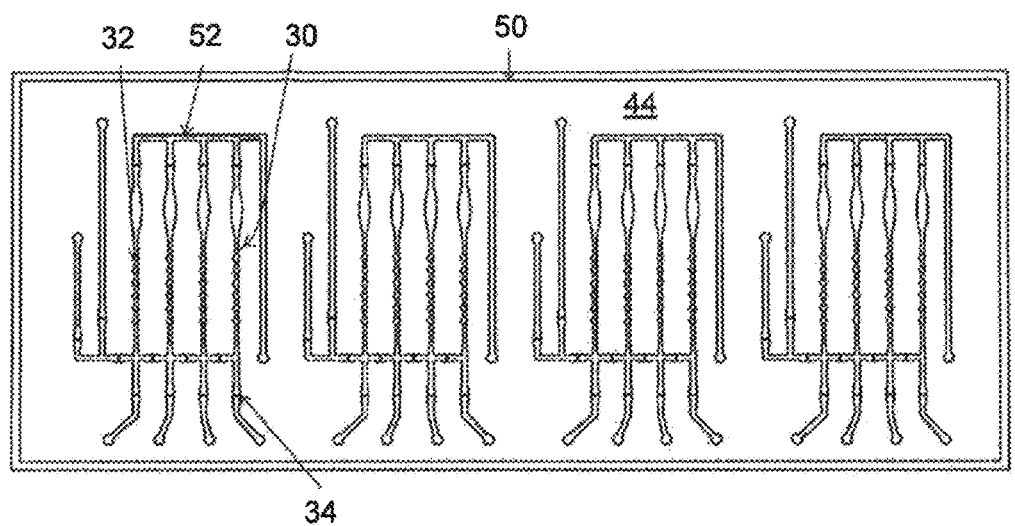
FIG. 14—A plan view of the fluidic sub-assembly of FIG. 9, on an enlarged scale.

FIG. 14 is a top view of the fluidic layer sub-assembly 48 with elements 32 in channels 30. The assembly 50 contains the elements.

In FIG. 14 four sets of microfluidic single sample, i.e., four analyte networks 52 are shown, each network is designed to perform an assay with its own respective sample.

FIG. 12 is a blowup schematic of a single channel 30 containing four elements 32 and microfluidic piston chamber 36, and valve 54 having seat 34, FIG. 10.

FIG. 12 depicts by arrowheads, flow through the bypass flowpath 41 around the hollow element 32 as well as through the element.

Referring to FIGS. 9 and 14, the channels 30 are formed by glass substrate 42 and micro-fluid channel walls formed by knife cutting sheet of PDMS of 110 micron thickness 32.

FIG. 9 shows forming the fluidic area 48 by bringing together glass sheet 42 and the unique cut-patterned PDMS sheet 42 using known techniques.

Reservoir/control plastic member 56 (containing fluidic reservoirs for sample, 22, assay buffer 24 and reagent waste 26) is bonded to PDMS membrane 38 to form control/reservoir layer 46.

Figure 15:
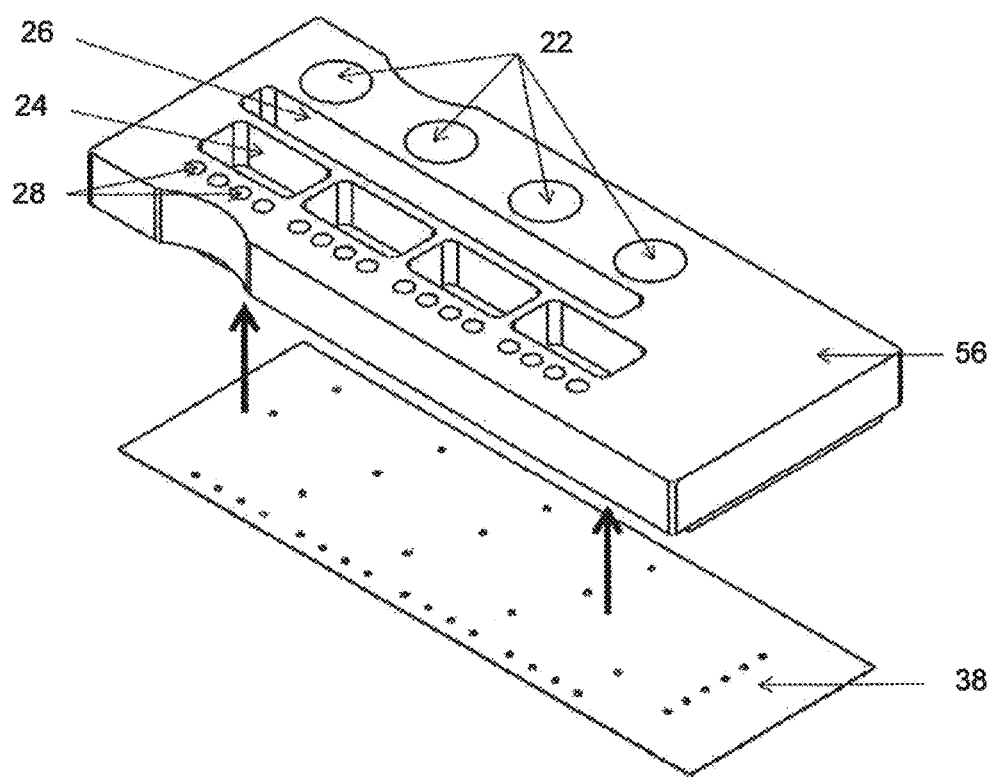
FIG. 15—A perspective view of parts of the pneumatic sub-assembly of FIG. 9, as they come together.
Figure 16:
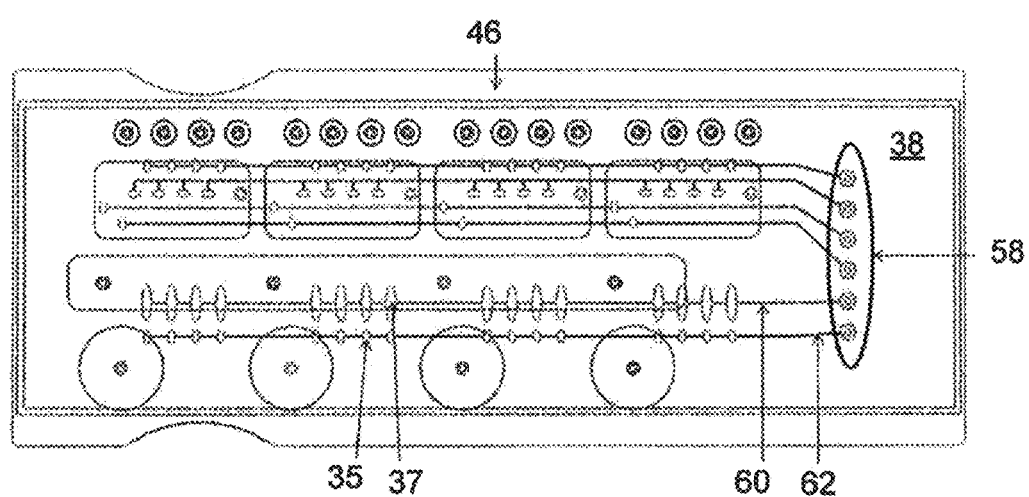
FIG. 16—A plan view, looking up at the underside of the pneumatic sub-assembly through its transparent membrane.
Figure 17:
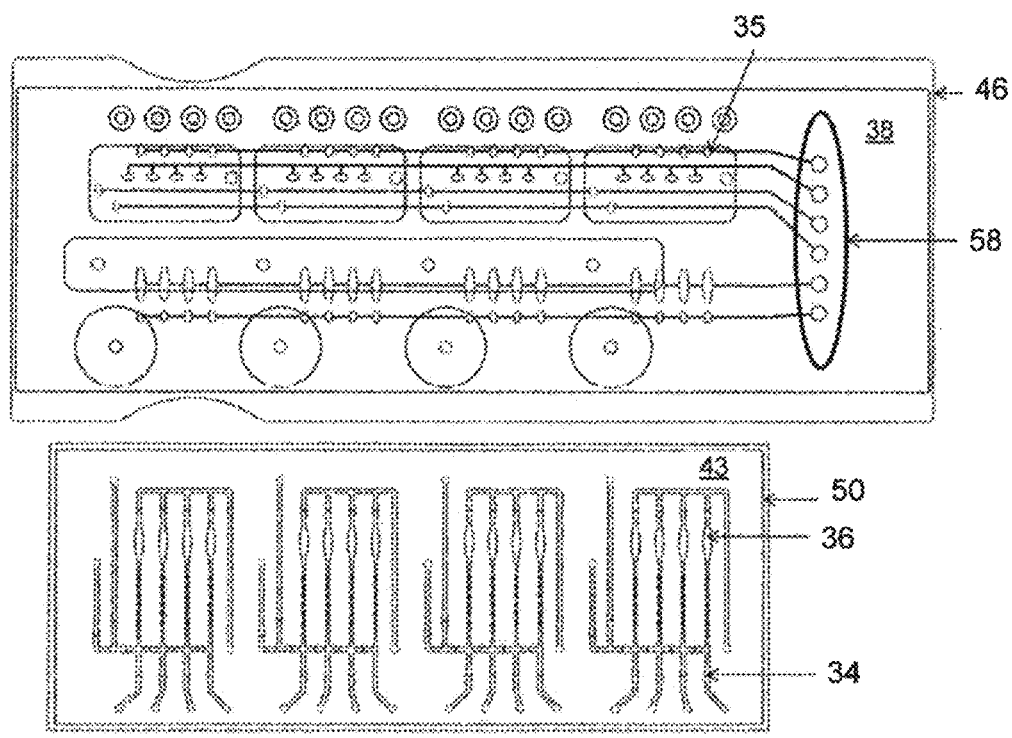
FIG. 17—A plan view, of the underside of the pneumatic sub-assembly and the mating upper surface of the fluidic sub-assembly.
Figure 18:
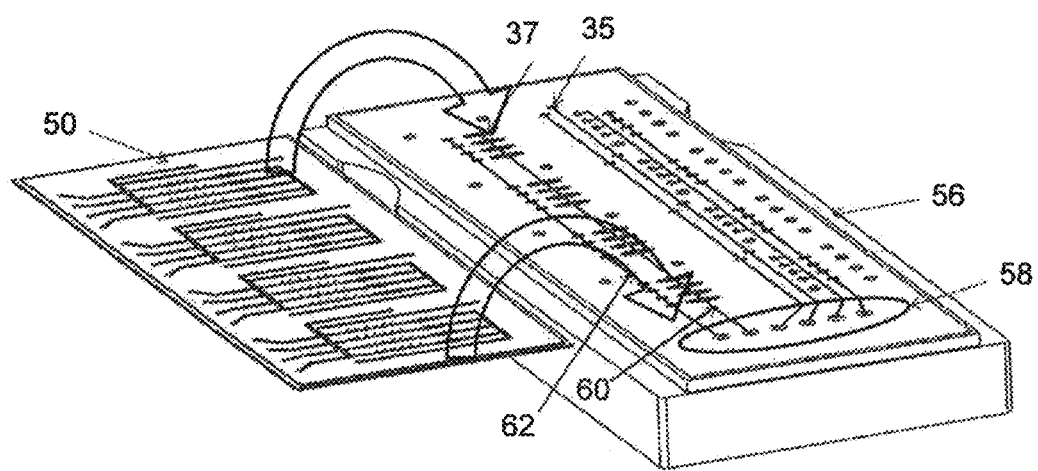
FIG. 18—A perspective view diagrammatically illustrating the mating action of the two sub-assemblies.
Figure 18A:
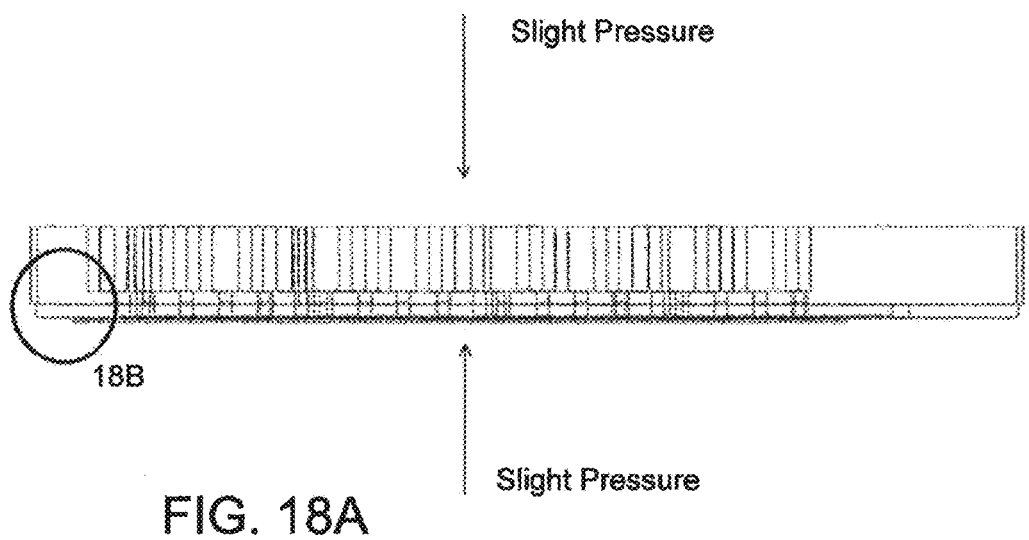
FIG. 18A—A side view illustrating the mating surface of the two subassemblies being pressed together with slight pressure.
Figure 18B:
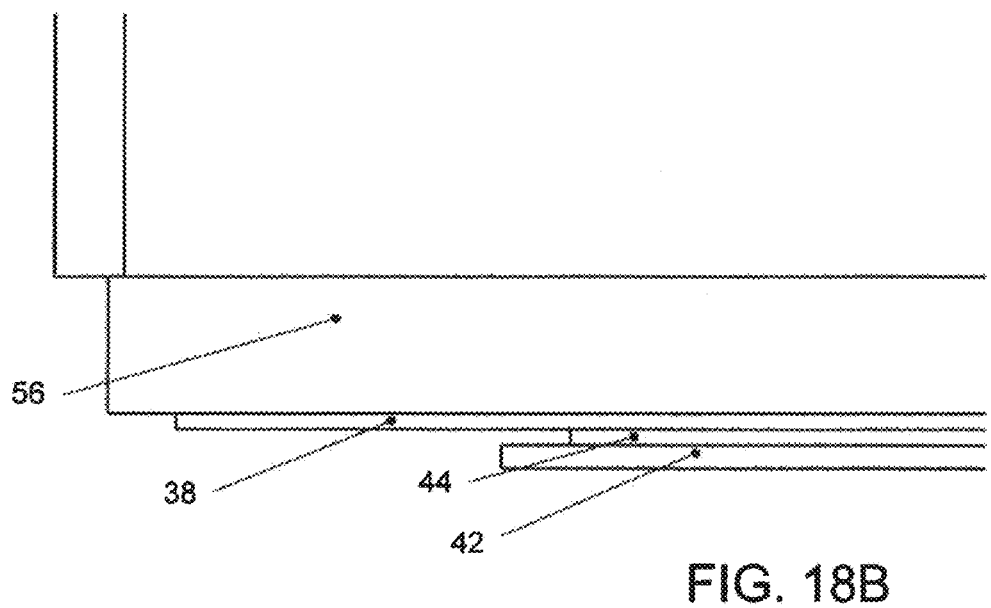
Figure 18C:
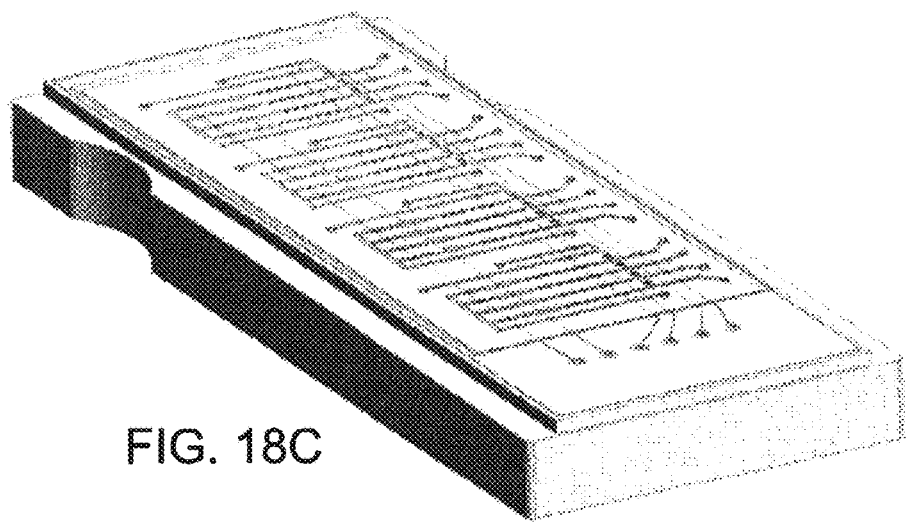
Figure 18D:
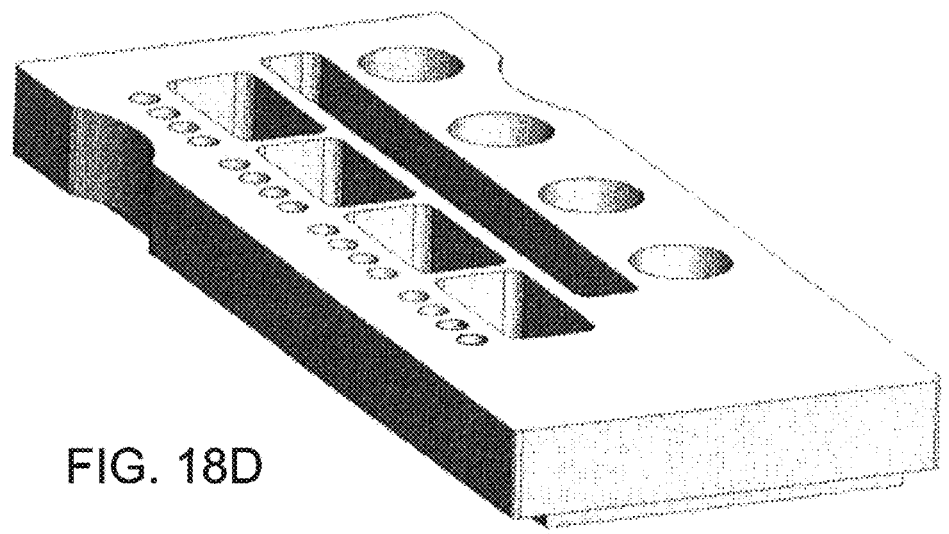
Figure 19:
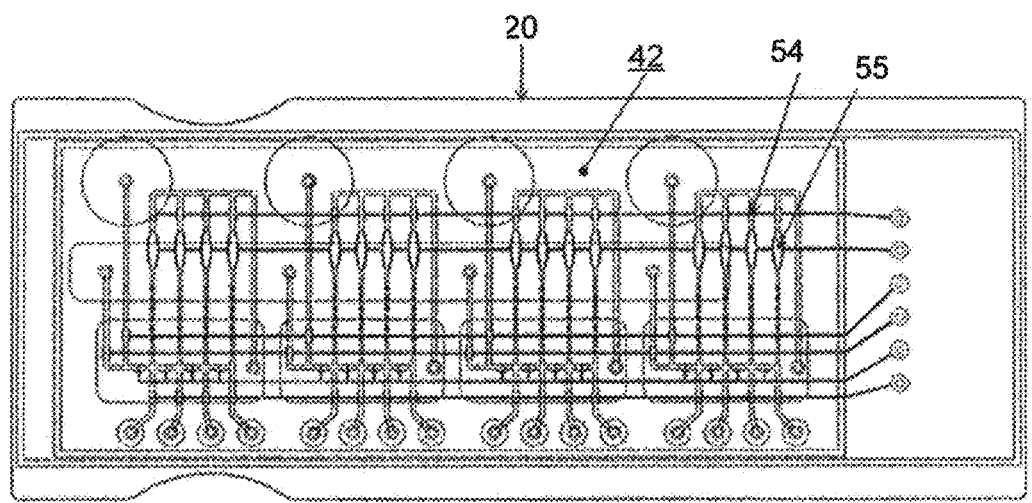
FIG. 19—A top view of the completed assembly.
Figure 20:
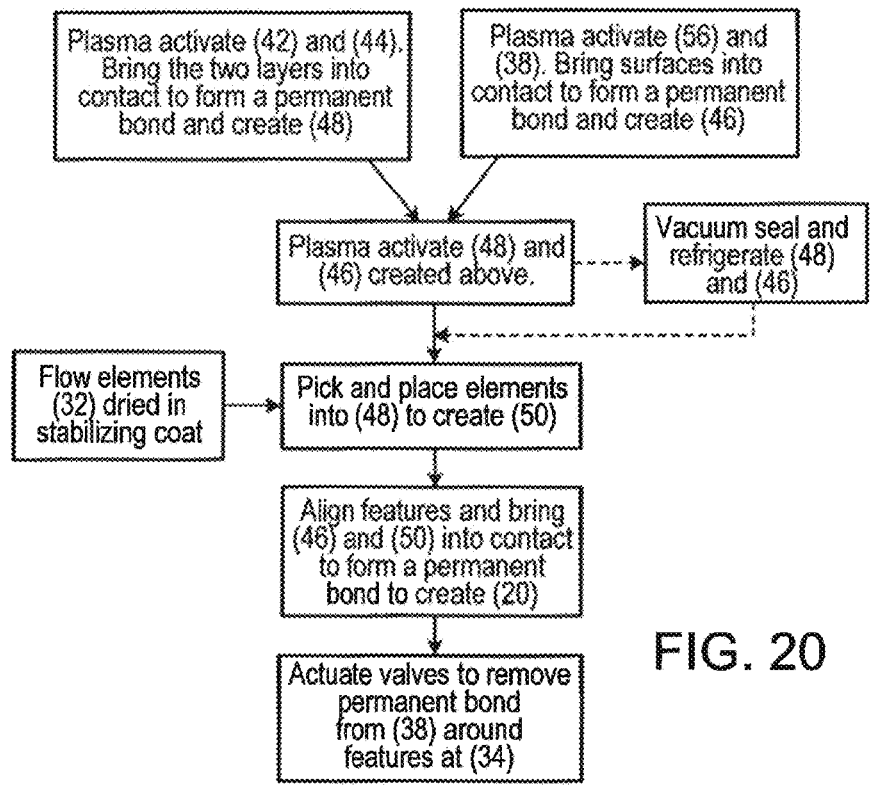
FIG. 20—A diagram of steps in the assembly process for the device of FIGS. 9, 9A, 10A, 10B, 10C, 11, 12, 12A, 12B, 12C, 12D, 12E, 12F, 12G, 13, 13A, 14, 15, 16, 17, 18, 18A, 18B, 18C, 18D, and 19.
Figure 20A:
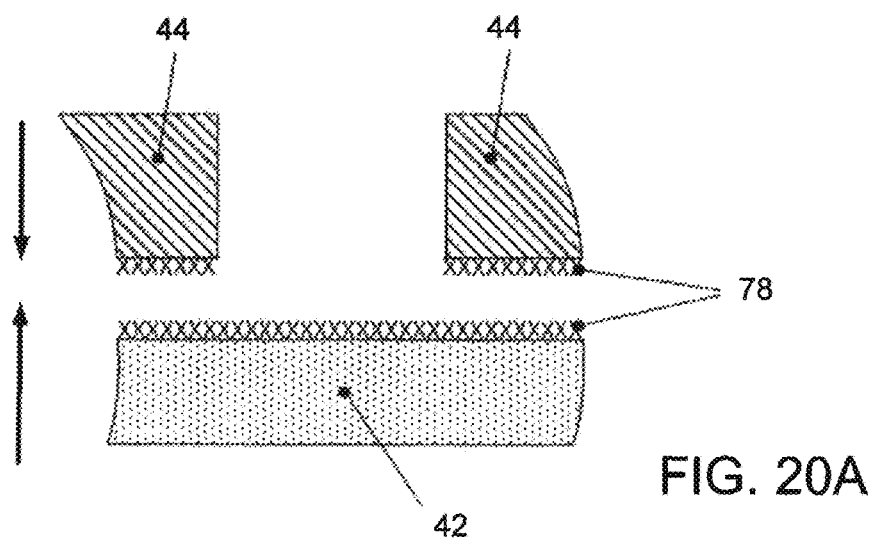
FIGS. 20A, 20B, 20C, and 20D—Illustrate steps in employing covalent bonding to form the liquid-tight channels and secure the extremely small hollow flow elements in place in the channels.
Figure 20B:
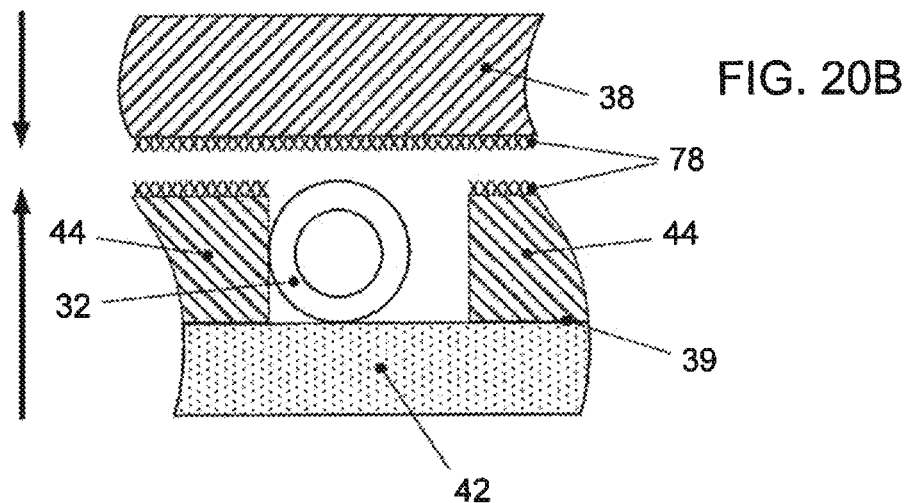
Figure 20C:
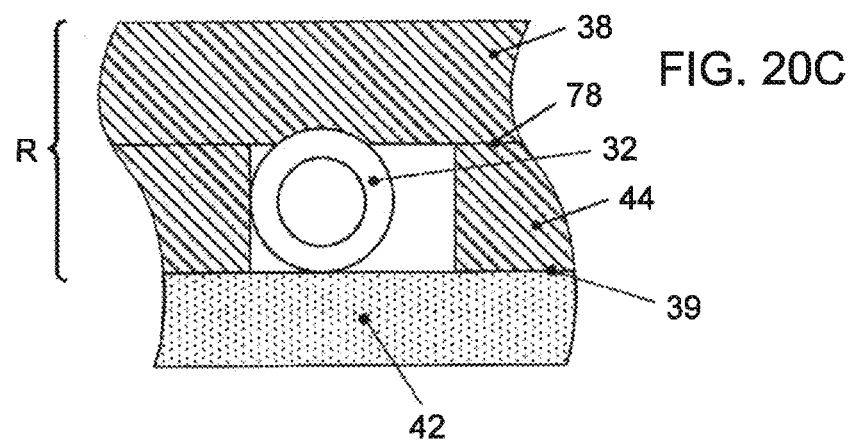
Figure 20D:
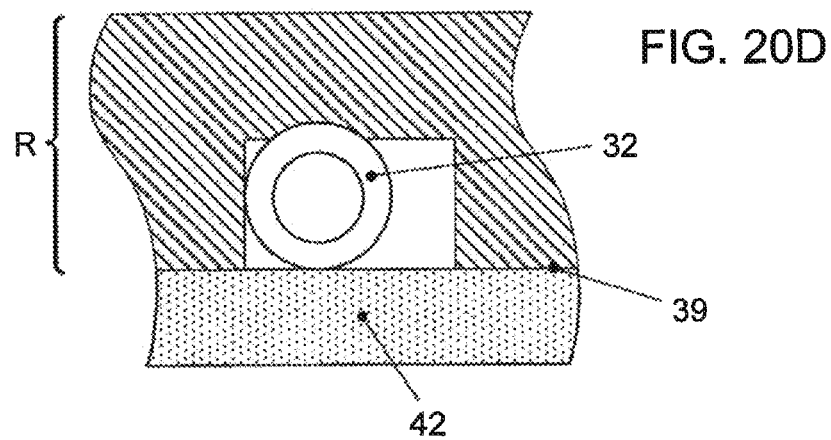
Figure 22:
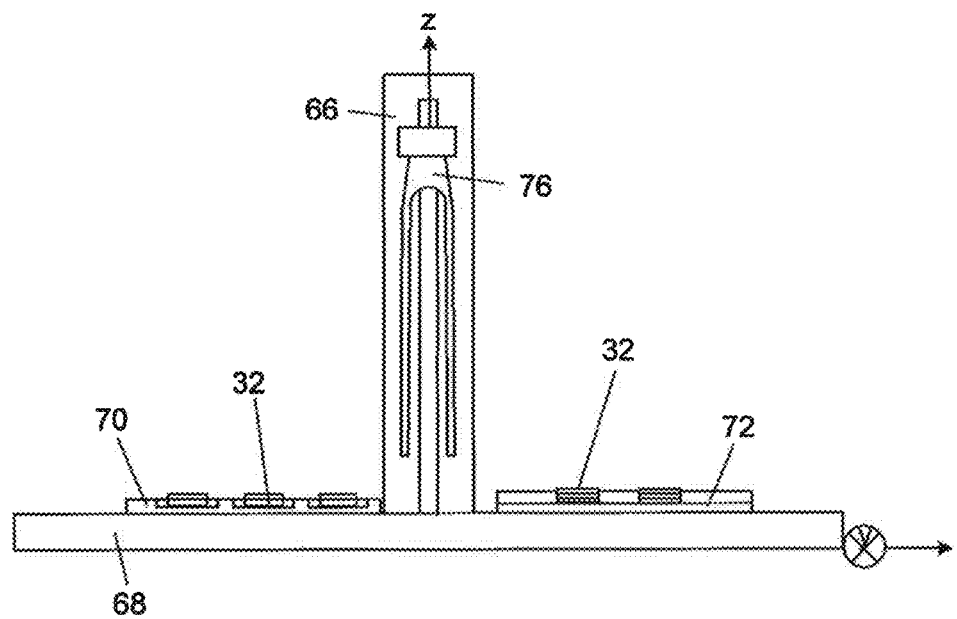
FIG. 22, A diagrammatic front view of a tweezer type pick and place device, and its support tower.
Figure 23:
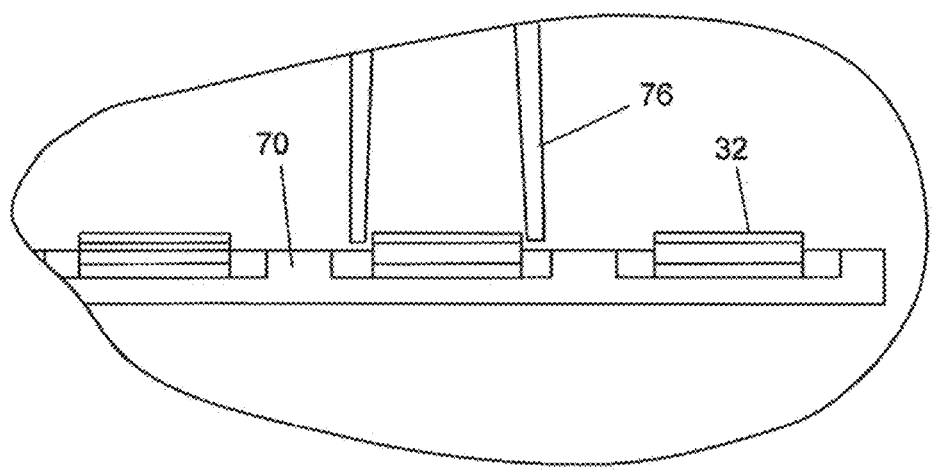
FIGS. 23 and 24—Respectively, picking and placing views of the device of FIGS. 21 and 22.
Figure 24:
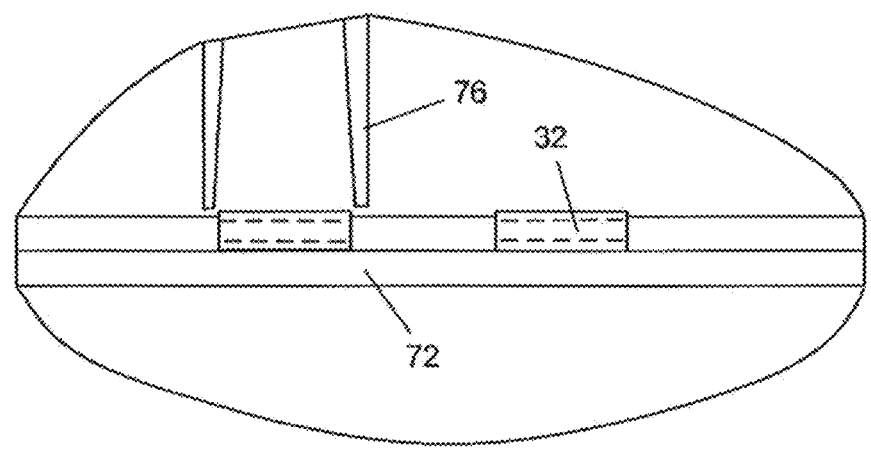
Figure 25:
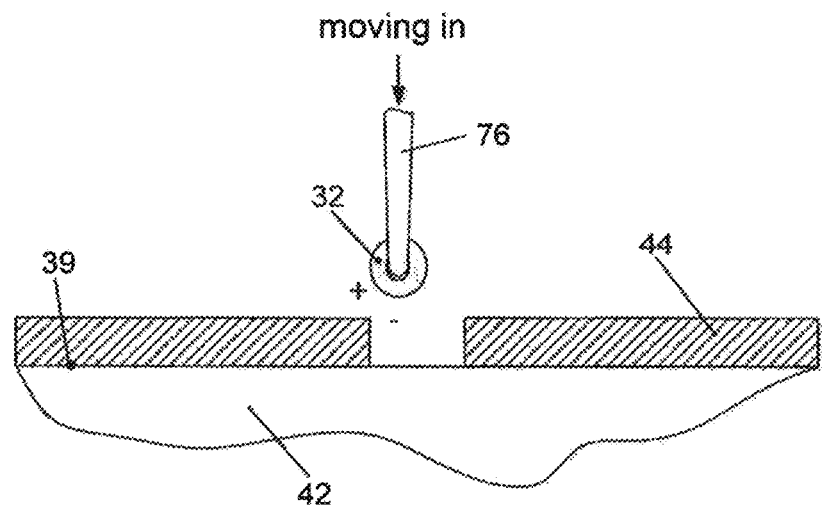
FIGS. 25, 26, and 27—A sequence of positions during placing of a flow element, diagrammatically illustrating the use of close-space electrostatic attraction between the channel wall and the element being delivered.
Figure 26:
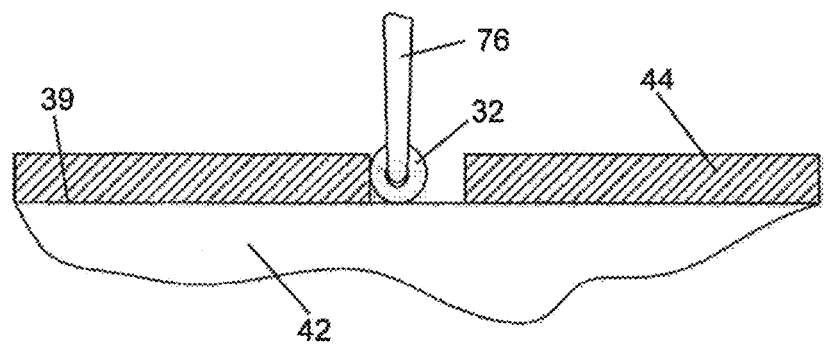
Figure 27:
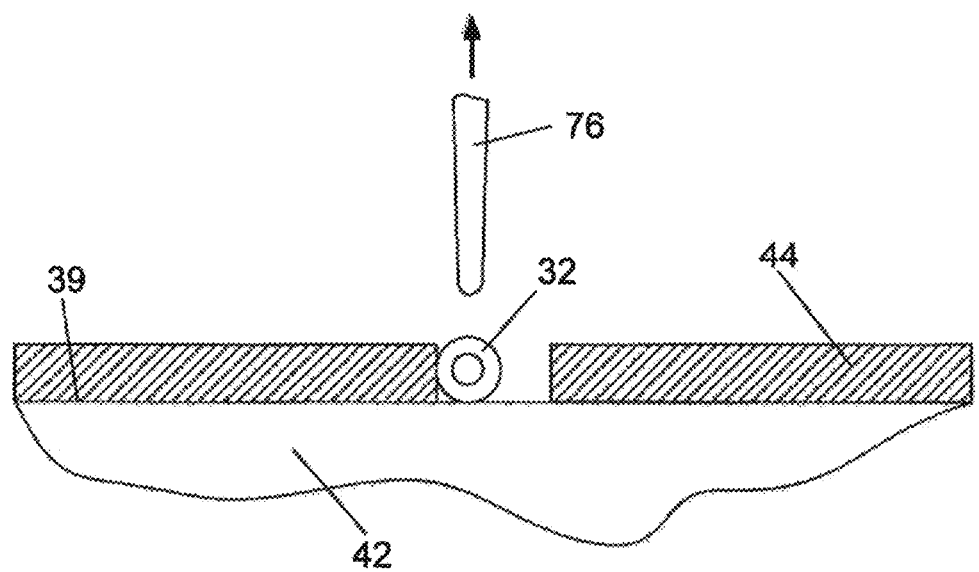
Figure 28:
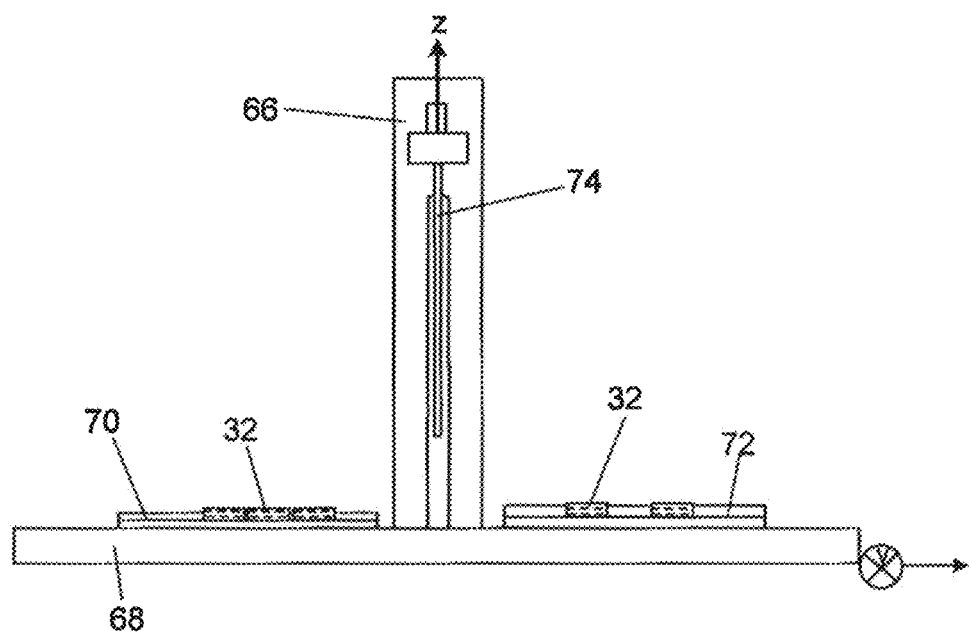
FIGS. 28, 29 and 30—Respectively, a front view, and picking and placing views of a vacuum pick up device.
Figure 29:
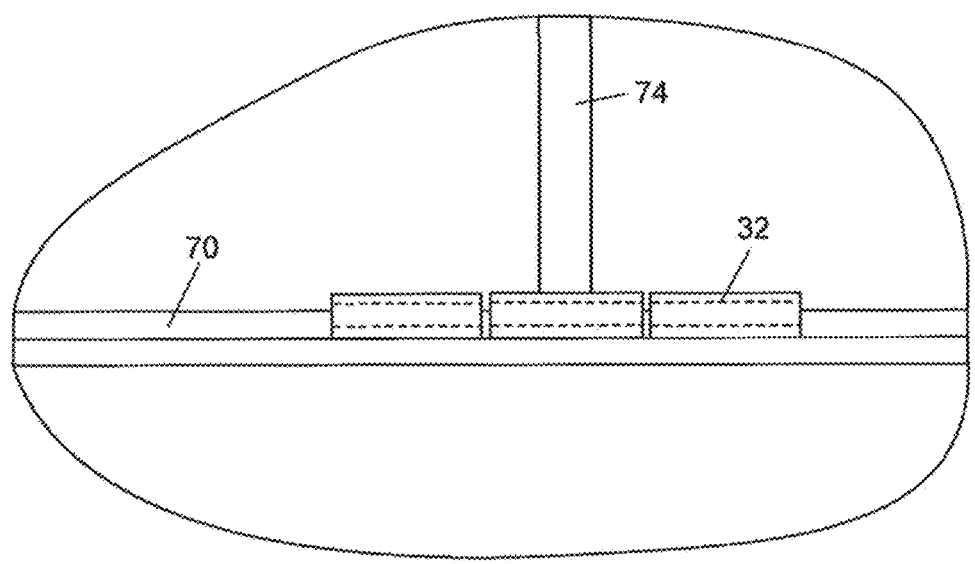
Figure 30:
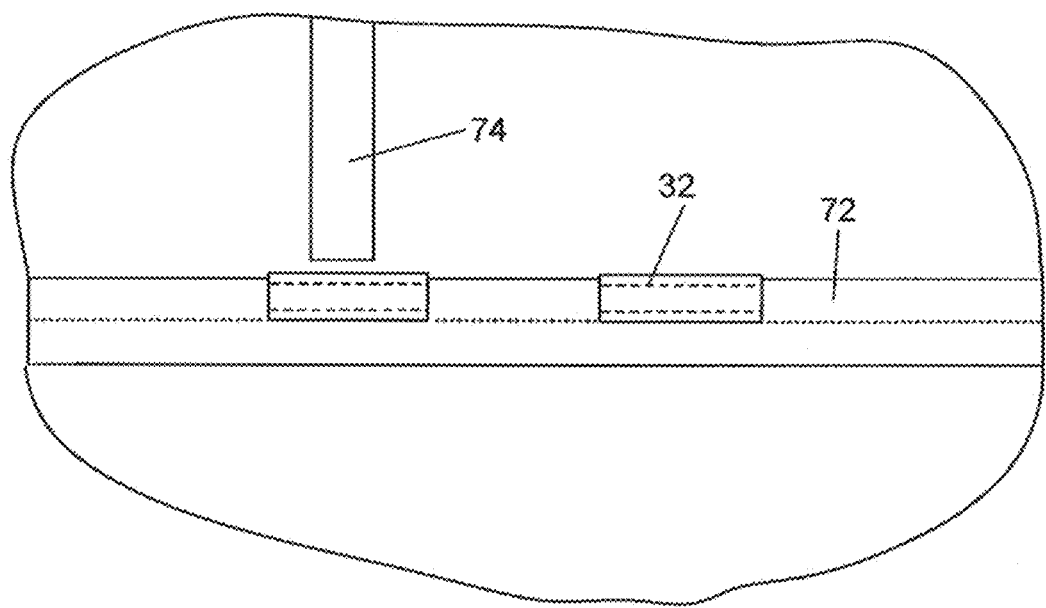
Figure 31:
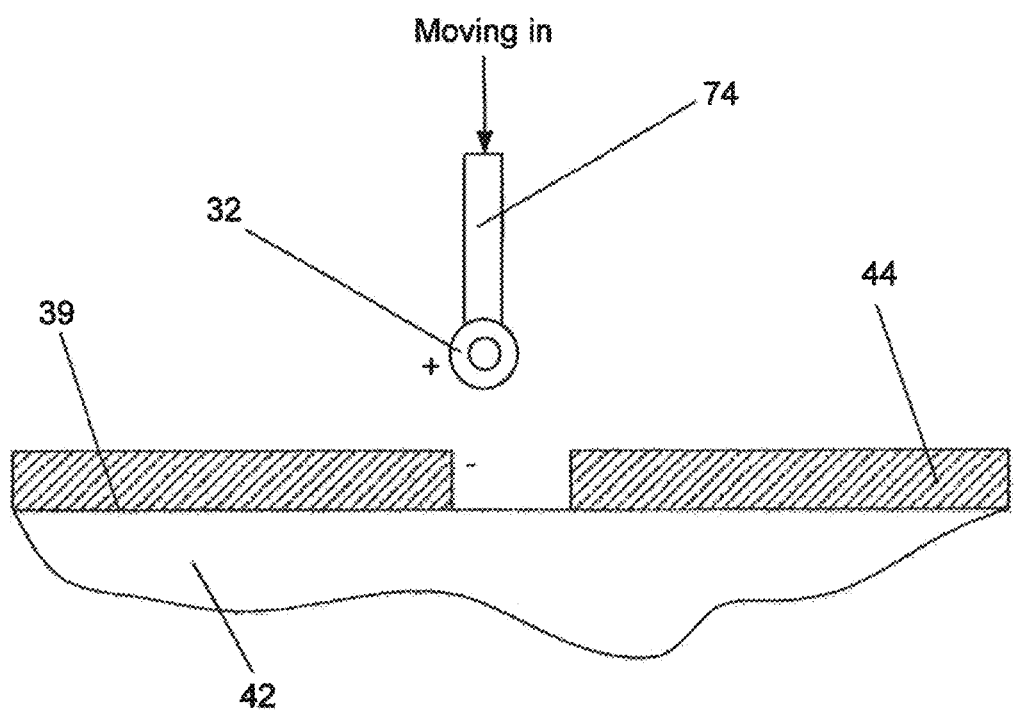
FIGS. 31, 32 and 33—A sequence of positions during placing of a flow element with the vacuum device, diagrammatically illustrating the use of close-space electrostatic attraction between the channel wall and the element being delivered.
Figure 32:
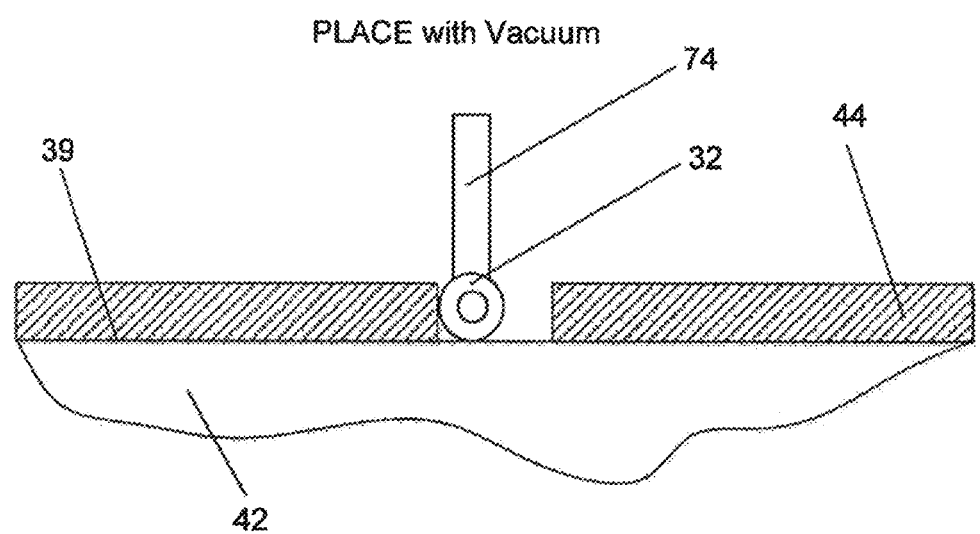
Figure 33:
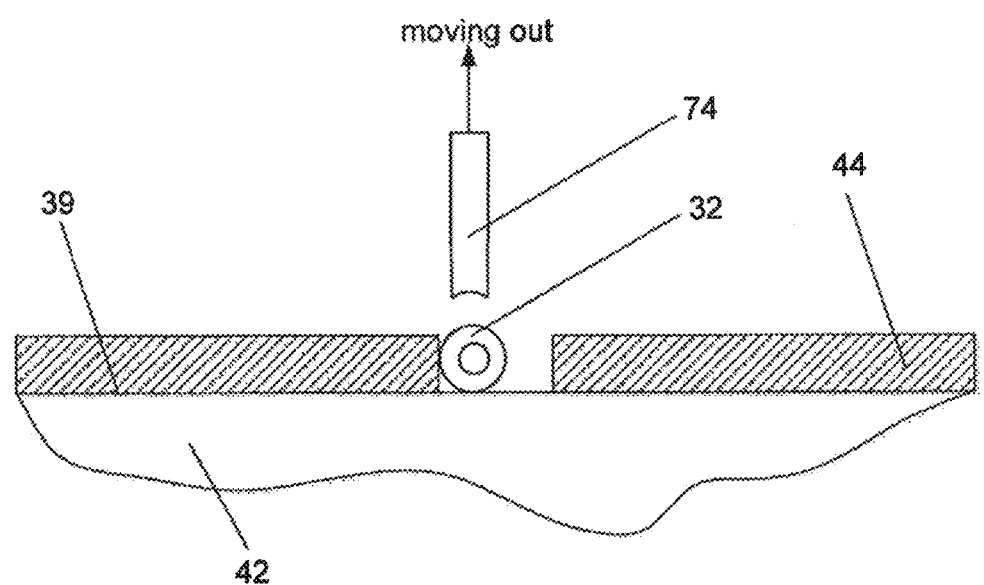
Figure 34:
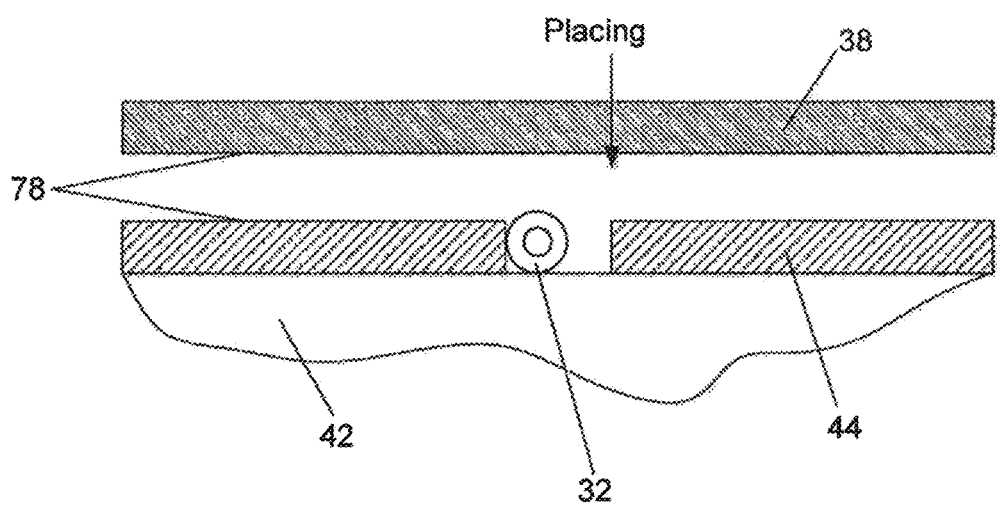
FIGS. 34 and 35—illustrate element-securing and channel-sealing actions occurring during assembly of the device of FIG. 9, et seq.
Figure 35:
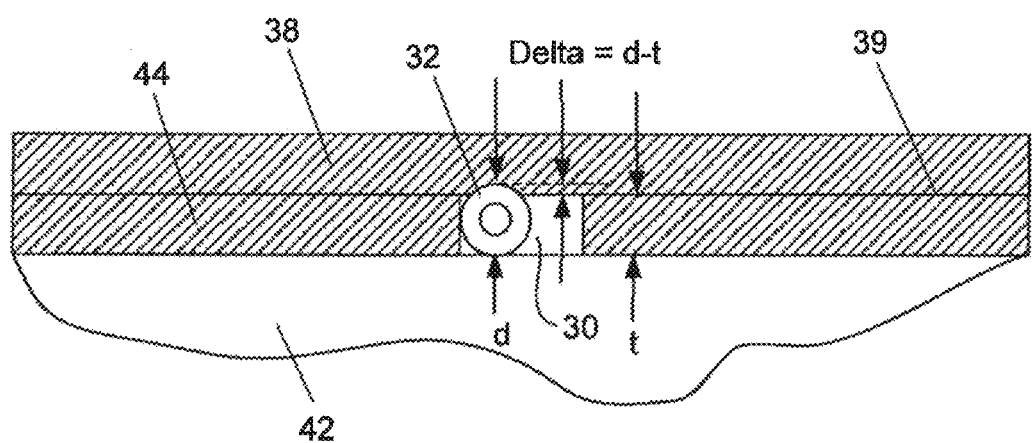
Figure 36:
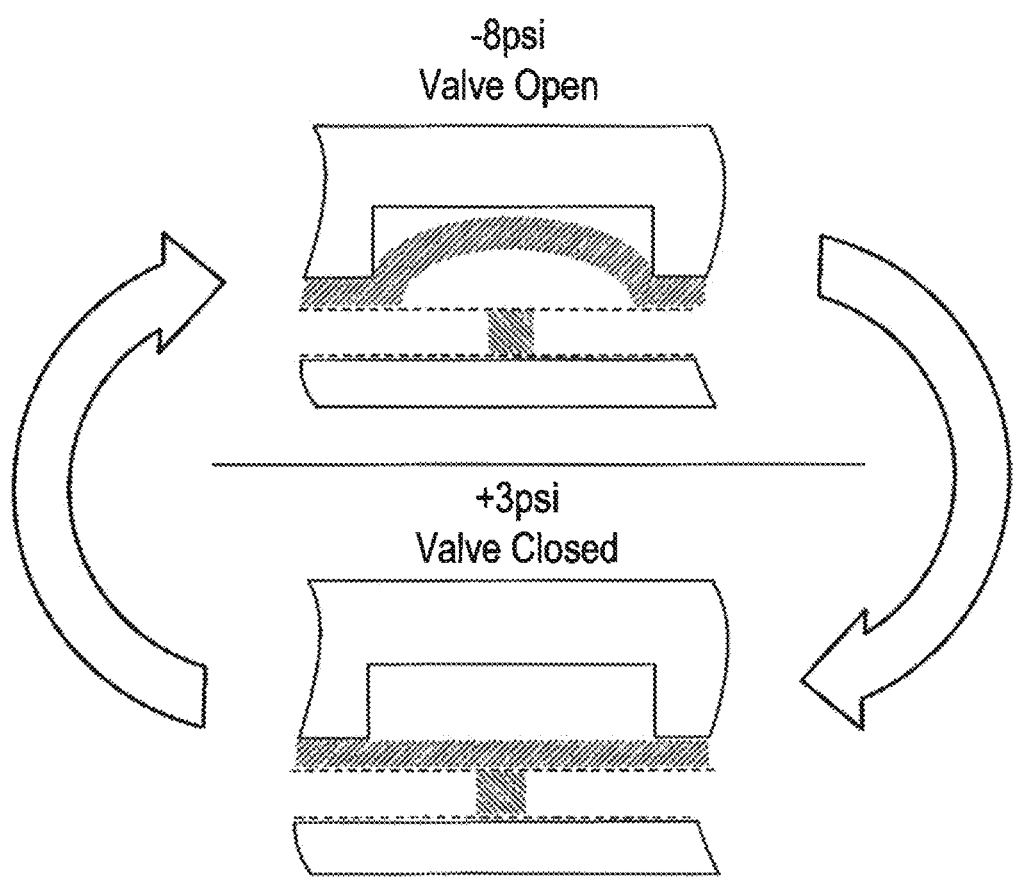
FIG. 36 is a diagrammatic view showing the repeated cycling of a diaphragm valve formed by an overlying portion of a PDMS layer, which is bonded to the opposed structure at each side, the valve, repeatedly closed with 3 psi positive pressure and opened with negative 8 psi pressure (vacuum), is found to overcome the molecular bonds being formed between diaphragm and valve seat, thus over time neutralizing the tendency for permanent co-valent bonds to form between contacting surface-activated surfaces, thus enabling the thus-formed valve to properly operate.
Figure 37:
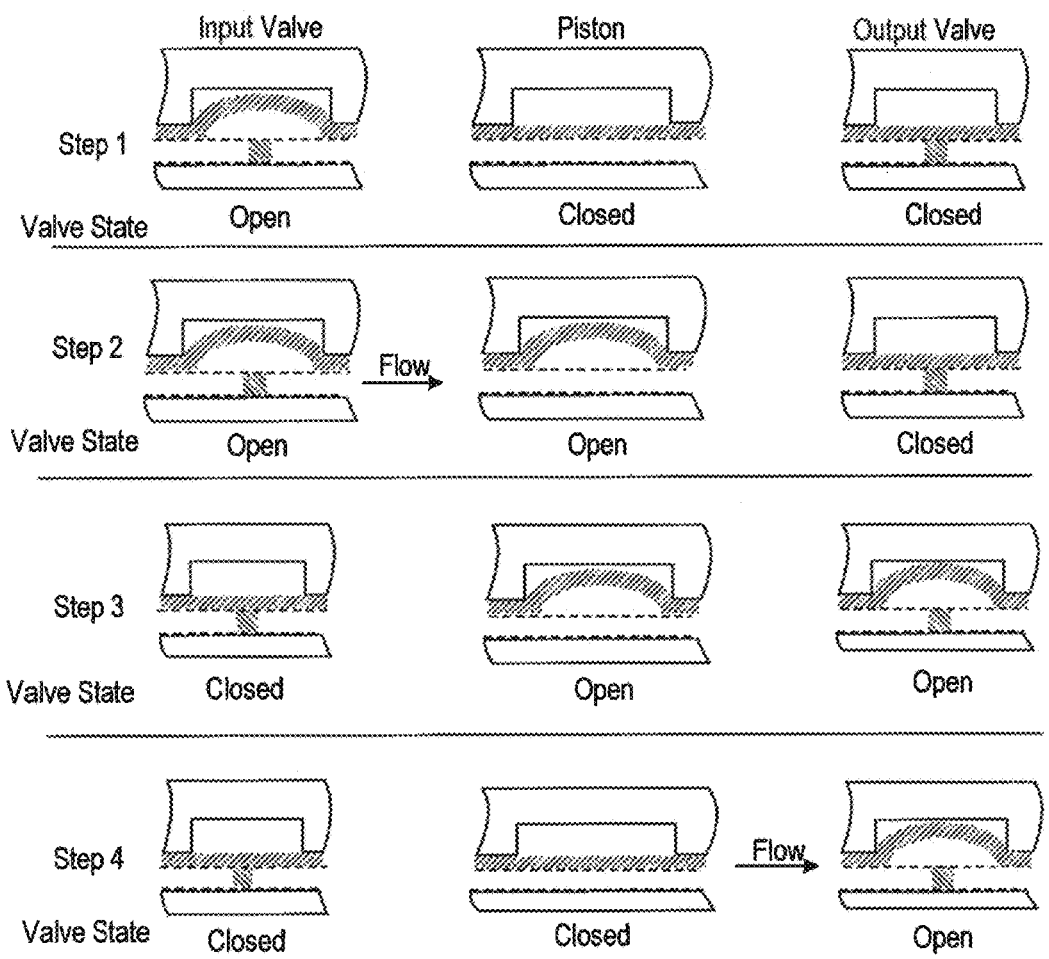
FIG. 37 pictures diagrammatically a pumping and valve state sequence by which liquid flow can be drawn into the piston from the left and expelled to the right to produce a desired directional, pulsating flow.

Referring to perspective of FIG. 15, layer 56 and membrane 38 are ready to be assembled by plasma-activated molecular bonding. FIG. 16 is a top view depicting final assembly 46. Pneumatic interface ports 58 are adapted to match with computer-controlled pneumatic control lines that provide pressure and vacuum actuation to valves 54 (formed by membrane 38 and microfluidic valve seat 34) and pistons 55 (the pistons being formed by elastomer membrane 38 lying over piston fluidic chamber 36 and piston pneumatic chamber) piston control lines 60 and valve control lines 62. The piston pump formed by membrane 38 sandwiched between 37 and 36 is activated by vacuum in one direction and pressure in the other.

A number of embodiments of the invention have been described. Nevertheless, it will be understood that various modifications may be made without departing from the spirit and scope of the invention. Accordingly, other embodiments are within the scope of the following claims.

What is claimed is:

1. A method of manufacturing a microfluidic device for performing a fluid assay, comprising: forming two subassemblies, each of the subassemblies having a backing of relatively rigid material and an oppositely directed face suitable for bonding to a mating face of the other subassembly, including inserting in fixed position into a microfluidic flow channel of one of the subassemblies at least one discrete reaction vessel in the form of a microlength hollow element, followed by bonding the subassemblies face-to-face.

2. The method of claim 1 including inserting the microlength hollow element into the microfluidic flow channel by pick-and-place motion.

3. The method of claim 2 in which the pick-and-place motion is effected by automated tweezer fingers engaging oppositely directed portions of the microlength hollow element.

4. The method of claim 2 in which close-field electrostatic attraction is employed to define a position of the microlength hollow element in the microfluidic channel and enable withdrawal of a placing instrument.

5. The method of claim 4 in which the microfluidic flow channel is of width greater than a width of the microlength hollow element and the electrostatic attraction employed is between the microlength hollow element and a side wall of the microfluidic flow channel.

6. The method of claim 5 in which the side wall is comprised of PDMS.

7. The method of claim 1 in which the microlength hollow element is provided on an inside surface of the microlength hollow element with a capture agent, including preparing the microlength hollow element by batch coating the microlength hollow element with the capture agent by mixing the microlength hollow element in a solution, and drying the microlength hollow element, and thereafter picking and placing the microlength hollow element in the flow microfluidic channel.

8. The method of claim 7 in which after the batch coating, an outside cylindrical surface of the microlength hollow element does not have any of the capture agent bound thereto.

9. The method of claim 8 in which, during the mixing in the solution, a fluid in the solution is agitated sufficiently to shear off any of the capture agent that has bound to the outside cylindrical surface of the microlength hollow element.

10. The method of claim 7, wherein the mixing produces a substantially uniform coating of the capture agent on the inside surface of the microlength hollow element.

11. The method of claim 7, wherein the assay comprises an immunoassay and the capture agent comprises an antibody.

12. The method of claim 1 in which the microlength hollow element has a length less than about 500 microns.

13. The method of claim 1 in which the microlength hollow element has a length of about 500 microns and an internal diameter of approximately 50 microns+/−25 microns.

14. The method of claim 1 in which the microlength hollow element has a length of about 250 microns.

15. The method of claim 1, in which a closure sheet is joined to a member defining the microfluidic flow channel containing the microlength hollow element by co-valent bonding of activated surfaces of bondable material, a contiguous portion of the closure sheet forming a flexible valve diaphragm that engages a valve seat originally formed of surface-activated bondable material, including subjecting the portion engaging the valve seat to a series of make-and-break contacts that interrupt covalent bonding of the valve diaphragm portion with the valve seat.

16. The method of claim 1, wherein the bonding comprises covalent bonding of selected regions of faces of surface-activated bondable materials.

17. The method of claim 16 wherein the faces of surface-activated bondable materials comprise surface-activated PDMS.

18. The method of claim 1, wherein the microfluidic device comprises microfluidic valves and pistons for moving fluid flow to perform the assay.

19. A method of manufacturing a microfluidic device for conducting a fluid assay, comprising:
  preparing at least one discrete reaction vessel in the form of a microlength hollow flow element in which the microlength hollow element is provided with a capture agent on an inside surface by batch coating the microlength hollow element by mixing the microlength hollow element in a solution, and agitating the solution sufficiently to shear off any of the capture agent that has bound to an outside cylindrical surface of the microlength hollow element;
  obtaining two subassemblies, each of the subassemblies having a backing of relatively rigid material and an oppositely directed face suitable for bonding to a mating face of the other subassembly;
  inserting the element in fixed position into a flow channel of one of the subassemblies; and
  bonding the two subassemblies face-to-face by covalent bonding selected regions of faces of surface-activated materials.

20. A method of manufacturing a microfluidic assay device, comprising:
  forming in a substrate, open fluid flow channels for flowing fluid of an assay;
  inserting in fixed position in at least one of the open fluid flow channels at least one discrete reaction vessel in the form of a microlength hollow flow element having a capture agent on an interior surface and not on an exterior cylindrical surface;
  covering the at least one of the open fluid flow channels and the microlength hollow flow element with a flexible sheet; and
  forming, with the flexible sheet, at selected regions of the at least one of the fluid flow channels away from the microlength hollow flow element, a flexible diaphragm of a microfluidic valve operable by pneumatic pressure.

\* \* \* \* \*